US008623365B2

(12) United States Patent
Davies et al.

(10) Patent No.: US 8,623,365 B2
(45) Date of Patent: Jan. 7, 2014

(54) Aβ BINDING MOLECULES

(75) Inventors: Julian Davies, La Jolla, CA (US); Ying Tang, San Diego, CA (US); Jeffry Dean Watkins, Encinitas, CA (US)

(73) Assignee: Applied Molecular Evolution, Inc., Indianapolis, IN (US)

( * ) Notice: Subject to any disclaimer, the term of this patent is extended or adjusted under 35 U.S.C. 154(b) by 211 days.

(21) Appl. No.: 13/332,753

(22) Filed: Dec. 21, 2011

(65) Prior Publication Data

US 2012/0114560 A1 May 10, 2012

Related U.S. Application Data

(63) Continuation of application No. 12/504,818, filed on Jul. 17, 2009, now Pat. No. 8,105,597, which is a continuation of application No. 10/544,050, filed as application No. PCT/US2004/002004 on Feb. 6, 2004, now Pat. No. 7,575,747.

(60) Provisional application No. 60/446,380, filed on Feb. 10, 2003.

(51) Int. Cl.
*A61K 39/395* (2006.01)

(52) U.S. Cl.
USPC ..................................... 424/145.1; 530/387.3

(58) Field of Classification Search
None
See application file for complete search history.

(56) References Cited

U.S. PATENT DOCUMENTS

| | | |
|---|---|---|
| 5,004,697 A | 4/1991 | Pardridge |
| 5,278,049 A | 1/1994 | Baker |
| 5,593,846 A | 1/1997 | Schenk |
| 5,688,651 A | 11/1997 | Solomon |
| 5,753,624 A | 5/1998 | McMichael |
| 5,766,846 A | 6/1998 | Schlossmacher |
| 5,837,672 A | 11/1998 | Schenk |
| 5,851,996 A | 12/1998 | Kline |
| 5,891,996 A | 4/1999 | Mateo de Acosta del Rio |
| 5,935,927 A | 8/1999 | Vitek |
| 6,114,113 A | 9/2000 | McLaughlin-Taylor |
| 6,114,133 A | 9/2000 | Seubert |
| 6,218,506 B1 | 4/2001 | Krafft |
| 6,284,221 B1 | 9/2001 | Schenk |
| 6,582,945 B1 | 6/2003 | Raso |
| 6,743,427 B1 | 6/2004 | Schenk |
| 2002/0009445 A1 | 1/2002 | Du |
| 2002/0058267 A1 | 5/2002 | Ozenberger |
| 2002/0086847 A1 | 7/2002 | Chain |
| 2002/0102261 A1 | 8/2002 | Raso |
| 2002/0136718 A1 | 9/2002 | Raso |
| 2004/0043418 A1 | 3/2004 | Holtzman |
| 2004/0192893 A1 | 9/2004 | Stavrianopoulos |
| 2004/0241164 A1 | 12/2004 | Bales |
| 2004/0248197 A1 | 12/2004 | Holtzman |
| 2004/0265308 A1 | 12/2004 | Schenk |
| 2005/0019330 A1 | 1/2005 | Schenk |

FOREIGN PATENT DOCUMENTS

| | | |
|---|---|---|
| EP | 0613007 | 8/1994 |
| EP | 0557270 B1 | 5/1995 |
| EP | 1257584 | 2/2001 |
| WO | 8901343 | 2/1989 |
| WO | 9618900 | 6/1996 |
| WO | 9625435 | 8/1996 |
| WO | 9833815 | 8/1998 |
| WO | 9834643 | 8/1998 |
| WO | 9844955 | 10/1998 |
| WO | 9906066 | 2/1999 |
| WO | 9927944 | 6/1999 |
| WO | 9960024 | 11/1999 |
| WO | 0072876 A2 | 12/2000 |
| WO | 0072880 A2 | 12/2000 |
| WO | 0077178 A1 | 12/2000 |
| WO | 0110900 A2 | 2/2001 |
| WO | 0118169 A2 | 3/2001 |
| WO | 0162801 A2 | 8/2001 |
| WO | 0221141 A2 | 3/2002 |
| WO | 0246237 A2 | 6/2002 |
| WO | 02060481 A1 | 8/2002 |
| WO | 02088307 | 11/2002 |
| WO | 03015617 A2 | 2/2003 |
| WO | 03015691 A2 | 2/2003 |
| WO | 03016466 A2 | 2/2003 |
| WO | 03016467 | 2/2003 |
| WO | 03090772 A1 | 11/2003 |

OTHER PUBLICATIONS

Haass, C., et al., "Amyloid beta-peptide is produced by cultured cells during normal metabolism," Nature, 359:322-325 (1992).
Ghiso, J., et al., "Epitope map of two polyclonal antibodies that recognize amyloid lesions in patients with Alzheimers disease," Biochem J, 282 (Pt 2):517-522 (1992).
Seubert, P., et al., "Isolation and quantification of soluble Alzheimer's β peptide from biological fluids," Nature, 359:325-327 (1992).
Gaskin, F., et al., "Human antibodies reactive with beta-amyloid protein in Alzheimer's disease," J Exp Med, 177(4):1181-1186 (1993).
Flood, JF, et al., "An amyloid β-protein fragment, Aβ [12-28], equipotently impairs post-training memory processing when injected into different limbic system structures," Brain Res, 663(2):271-276 (1994).
Koudinov, A., et al., "The soluble form of Alzheimer's amyloid beta protein is complexed to high density lipoprotein 3 and very high density lipoprotein in normal human plasma," Biochem & Biophysic Res Comm, 205:1164-1171 (1994).
Schwarzman, AL et al., "Transthyretin sequesters amyloid β protein and prevents amyloid formation," Proc Natl Acad Sci, 91:8368-8372, (1994).
Tabaton, M., et al., "Soluble amyloid β-protein is a marker of Alzheimer amyloid in brain but not in cerebrospinal fluid," Biochem and Biophysi Res Comm, 200(3):1598-1603 (1994).

(Continued)

*Primary Examiner* — Gregory S Emch
(74) *Attorney, Agent, or Firm* — Sanjay Jivraj

(57) ABSTRACT

The present invention encompasses isolated antibodies, or fragments thereof, that are humanized variants of murine antibody 266 which employ complementarity determining regions derived from murine antibody 266. The variant antibodies are useful for treatment or prevention of conditions and diseases associated with Aβ, including Alzheimer's disease, Down's syndrome, cerebral amyloid angiopathy, mild cognitive impairment, and the like.

16 Claims, No Drawings

(56) References Cited

OTHER PUBLICATIONS

Walker, LC et al., "Labeling of cerebral amyloid in vivo with a monoclonal antibody," J Neuropathol Exp Neurol, 53(4):377-383 (1994).
Wisniewski, T., et al., "Alzheimer's disease and soluble A beta," Neurobiol Aging, 15(2):143-52 Review (1994).
DeMattos, R.B., et al., "Brain to Plasma Amyloid-β Efflux: a Measure of Brain Amyloid Burden in a Mouse Model of Alzheimer's Disease," Science, 295, pp. 2264 2267 (2002).
Giulian, D., et al., "Specific domains of β-amyloid from Alzheimer plaque elicit neuron killing in human microglia," J Neurosci, 16 (19):6021-6037 (1996).
Hanan, E., et al., "Inhibitory effect of monoclonal antibodies on Alzheimer's βamyloid peptide aggregation," Int J Exp Clin Invest, 3:130-133 (1996).
Solomon, B., et al., "Monoclonal antibodies inhibit in vitro fibrillar aggregation of the Alzheimer beta-amyloid peptide," Proc Natl Acad Sci USA, 93(1):452-5 (1996).
Teller, JK et al., "Presence of soluble amyloid β-peptide precedes amyloid plaque formation in Down's syndrome," Nature Medicine, 2(1)93-95 (1996).
Tjernberg, LO et al., "Arrest of beta-amyloid fibril formation by a pentapeptide ligand," J Biol Chem, 271(15):8545-8548 (1996).
Winter G., et al., "Humanized antibodies" Immunology Today, 14(6):243-246 (1996).
Solomon, B., et al., "Disaggregation of Alzheimer beta-amyloid by site-directed mAb," Proc Nat Acad Sci USA, 94(8):4109-4112 (1997).
El-Agnaf, OM et al., "The influence of the central region containing residues 19-25 on the aggregation properties and secondary structure of Alzheimer's beta-amyloid peptide," Eur J Biochem, 256(3):560-569 (1998).
He X-Y et al., "Humanization and pharmacokinetics of a monoclonal antibody with specificity for both E- and P-selectin," J Immunol, 160:1029-1035 (1998).
Lambert, MP et al., "Diffusible, nonfibrillar ligands derived from Aβ 1-42 are potent central nervous system neurotoxins," Proc Natl Acad Sci, 95:6448-6453 (1998).
Solomon, B., et al., The amino terminus of the β-amyloid peptide contains an essential epitope for maintaining its solubility, Progress in Alzheimer's and Parkinson's Diseases, 205-211 (1998).
Soto, C., et al., "1-sheet breaker peptides inhibit fibrillogenesis in a rat brain model of amyloidosis: Implications of Alzheimer's therapy," Nature Medicine, 4(7):822-826 (1998).
Blass, JP, "Immunologic treatment of Alzheirner's disease," NEJM, 341:1694-1695 (1999).
Kuo, YM et al "High levels of circulating Abeta42 are sequestered by plasma proteins in Alzheimer's disease," Biochem Biophys Res Commun, 257(3):787-791 (1999).
McLean, C., et al., "Soluble pool of AP amyloid as a determinant of severity of neurodegeneration in Alzheimer's disease," Amer Neurological Assoc, 46:860-866 (1999).
Schenk, D., et al., "Immunization with amyloid-β attenuates Alzheimer-disease-like pathology in the PDAPP mouse," Nature, 400:173-177 (1999).
St. George-Hyslop, P., et al., "Antibody clears senile plaques" Nature, 400:116-117 (1999).
Wang, J., et al., "The levels of soluble versus insoluble brain AP distinguish Alzheimer's disease from normal and pathologic aging," Experimental Neurology, 158:328-337 (1999).
Bard, F., et al., "Peripherally administered antibodies against amyloid beta-peptide enter the central nervous system and reduce pathology in a mouse model of Alzheimer disease," Nat Med, 6(8):916-919 (2000).
Games, D., et al., "Prevention and reduction of AD-type pathology in PDAPP mice immunized with Aβ1-42," Annals of NY Acad Sci, 920:274-284 (2000).
Levy A., et al., "Immunization for Alzheimer's disease: A shot in the arm or a whiff?" American Neurological Assoc, 48:553-555 (2000).
Janus, C., et al., "Aβ peptide immunization reduces behavioural impairment and Plaques in a model of Alzheimer's disease," Nature, 408:979-982 (2000).
Morgan, D., et al., "Aβ peptide vaccination prevents memory loss in an animal model of Alzheimer's disease," Nature, 408:982-985 (2000).
Naslund, J., et al., "Correlation between elevated levels of amyloid β peptide in the brain and cognitive decline," J Am Med Assoc, 283:1571 (2000).
Zlokovic, B.V., et al., "Clearance of amyloid β-peptide from brain: transport or metabolism?" Nature Medicine, 6(7) 718-719 (2000).
Arendash, GW, et al., "Behavioral assessment of Alzheimer's transgenic mice following long-term AP3 vaccination: Task specificity and correlations between Aβ deposition and spatial memory," DNA and Cell Biology, 20(11):737-744 (2001).
Bacskai, BJ, et al., "Imaging of amyloid-β deposits in brains of living mice permits direct observation of clearance of plaques with immunotherapy," Nature Medicine, 7(3):369-372 (2001).
DeMattos, R.B., et al., "Peripheral anti-Aβ antibody alters CNS and plasma AP clearance and decreases brain Aβ burden in a mouse model of Alzheimer's disease," PNAS, 98(15):8850-8855 (2001).
Bard, Frederique, et al., "Peripherally administered antibodies against amyloid β-peptide enter the central nervous system and reduce pathology in a mouse model of Alzheimer's disease," Nature Medicine, 6(8), 916-919 (2000).
Dickey, CA, et al., Duration and specificity of humoral immune responses in mice vaccinated with the Alzheimer's disease-associated β-amyloid 1-42 peptide, DNA and Cell Biology, 20(11):723-729 (2001).
Esiri, MM, et al., "Is an effective immune intervention for Alzheimer's disease in prospect?" Trends Pharmacol Sci, 22(1):2-3 (2001).
Haass, C., et al., "Protofibrils, the unifying toxic molecule of neurodegenerative Disorders?" Nature Neuroscience, 4(9):859-860 (2001).
Klein, WL, et al., "Targeting small AP oligomers: the solution to an Alzheimer's disease conundrum?" Trends in Neurosciences, 24(4):219-224 (2001).
Lambert, MP, et al., "Vaccination with soluble AP oligomers generates toxicity neutralizing antibodies," J Neurochem, 79:595L605 (2001).
Lee, VM-Y, et al., "AP immunization: Moving AO peptide from brain to blood," PNAS, 98(16), pp. 8931-8932 (2001).
Poduslo, JF, et al., "Permeability of proteins at the blood-brain barrier in the normal adult mouse and double transgenic mouse model of Alzheimer's disease," Neurobiol Dis, 8(4):555-567 (2001).
Town, T., et al., "Characterization of murine immunoglobulin G antibodies against human amyloid-β1-42," Neuroscience Letters, 307:101-104 (2001).
DeMattos R.B., et al., "Plaque-associated disruption of CSF and plasma amyloid-P(AP) equilibrium in a mouse model of Alzheimer's disease," J Neurochem, 81:229-236, (2002).
Kotilinek, L.A., et al., "Reversible memory loss in a mouse transgenic model of Alzheimer's disease," J Neurosci, 22(15):6331-6335 (2002).
Wang, H-W, et al., "Soluble oligomers of β amyloid (1-42) inhibit long-term potentiation but not long-term depression in rate dentate gyrus," Brain Research, 924:133-140 (2002).
Strbak, V., et al, "Passive Immunization and Hypothalamic Peptide Secretion," Neuroendocrinology, 58:210-217 (1993).
Ragusi, C., et al., "Redistribution of Imipramine from Regions of the Brain Under the Influence of Circulating Specific Antibodies," J. Neurochem., 70(5), pp. 2099-2105 (1998).
Suo, Z., et al., "Soluble Alzheimers β-amyloid constricts the cerebral vasculature in vivo" Neuroscience Letters 257, pp. 77-80 (1998).
Lue, L., et al., "Soluble β-amyloid Peptide Concentration as a Predictor of Synaptic Change in Alzheimer's Disease," Am. J. PatholL, 155: pp. 853-862 (1999).
Teller, J., et al., "Presence of soluble amyloid β-peptide precedes amyloid plague formation in Down's syndrome," Nature Medicine, vol. 2, No. 1, pp. 93-95 (1996).

(56) References Cited

OTHER PUBLICATIONS

Esler, W., et al., "Point substitution in the central hydrophobic cluster of a human β-amyloid congener disrupts peptide folding and abolishes plaque competence," Biochemistry, vol. 35, pp. 13914-13921 (1996).

Maggio, J. & Mantyh, P. "Brain Amyloid—A Physicochemical Perspective" Brain Pathology, vol. 6,147-162 (1996).

Gorevic, P., et al. "Ten to fourteen residue peptides of Alzheimer's disease protein are sufficient for amyloid fibril formation and its characteristic X ray diffraction pattern" Biochem. and Biophy Res. Commun., vol. 147, No. 2 (1987).

Balbach, J., et al. "Amyloid fibril formation by Aβl6-22, a seven-residue fragment of the Alzheimer's P-amyloid peptide, and structural characterization by solid state NMR" Biochemistry, vol. 39, pp. 13748-13759 (2000).

Simmons, L., "Secondary structure of amyloid β peptide correlates with neurotoxic activity In Vitro" Molecular Pharmacology, vol. 45, pp. 373-379 (1994).

Wood, A., et al., "Prolines and amyloidogenicity in fragments of the Alzheimer's peptide β/A4", Biochemistry, vol. 34, pp. 724-730 (1995).

Xu, S. and Gaskin F. "Increased incidence of anti-β-amyloid autoantibodies secreted by Epstein-Barr virus transformed B cell lines from patients with Alzheimer's disease" Mechanisms of Ageing and Development, vol. 94, pp. 213-222 (1997).

Soto, C., et al., "The a-helical to β-strand transition in the amino-terminal fragment of the amyloid f-peptide modulates amyloid formation" J. Biol. Biol. Chem, vol. 270, No. 7, pp. 3063-3067 (1995).

Tjernberg, L., et al., "A molecular model for Alzheimer amyloid β-peptide fibril formation," J Biol. Chem, vol. 274, No. 18, pp. 12619-12625 (1999).

Hilbich, C., et al., "Substitutions of hydrophobic amino acid reduce the amyloidogenicity of Alzheimer's disease βA4 peptides," J. Mol. Biol., vol. 228, pp. 460-473 (1992).

Hilbich, C., et al., "Human and rodent sequence analogs of Alzheimer's amyloid βA4 share similar properties and can be solubized in buffers of pH 7.4" Eur. J. Biochem., vol. 201, pp. 61-69(1991).

Pillot, T., et al., "Fusogenic Properties of the C-terminal Domain of the Alzheimer β-Amyloid Peptide" J. Biol Chem., vol. 271, No. 24, pp. 28757-28765 (1996).

Dodart, JC, et al, "Immunization reverses memory deficits without reducing brain Aβ burden in Alzheimer's disease model," Nature Neuroscience, vol. 5(5) 452-457 (2002).

Shibata, et al., "Clearance of Alzheimer's Amyloid-β1-40 peptide from brain by LDL receptor-related protein-lat the blood-brain barrier," J. Clin. Invest, 106:1489-1499 (2000).

Zlokovic, et al., "Blood-Brain Barrier Transport of Circulating Alzheimer's," Biochem. Biophys. Res. Comm., 197(3):1034-1040 (1993).

Racke, et al., "Exacerbation of Cerebral Amyloid Angiopathy-Associated Microhemorrahage in amyloid Precursor Protein Transgenic Mice by Immunotherapy Is Dependent on Antibody Recognition of Deposited Forms of Amyloid β," J. Neurosic. , 19:25(3):629-636 (2005).

Legleiter, et al., "Effect of Different Anti-Aβ Antibodies on Aβ Fibrillogenesis as Assessed by Atomic force Microscopy," J. Mol. Biol. 23:335(4):997-1006 (2004).

Gavel, et al., "Sequence differences between glycosylated and non-glycosylated Asn-X-Thr/Ser acceptor sites: implications for protein engineering," Protein Engineering, vol. 3(5), 433-442, (1990).

Co, M.S., et al., "Genetically Engineered Deglycoslation of the Variable Domain Increases the Affinity of an Anti-CD33 Monoclonal Antibody," Molecular Immuno.,vol. 30(15) 1361-1367 (1993).

Wallick, S.C., et al., "Glycosylation of a VH Residue of a Monoclonal Antibody Against β(1-6) Dextran Increases Its Affinity for Antigen," J. Exp Med., vol. 168, 1099-1109 (1988).

Hilbich, C., et al., "Aggregation and secondary structure of synthetic amyloid βA4 peptides of Alzheimer's disease" J. Mol. Biol., vol. 218, pp. 149-163 (1991).

Lee, VM-Y, et al., "Aβ immunization: Moving Aβ peptide from brain to blood," PNAS, vol. 98(16) 8931-8932 (2001).

Levitt, M., "Molecular dynamics of native protein," J Mol Biol, 168:595-620 (1983).

Queen, C., et al., "A humanized antibody that binds to the interleukin 2 receptor," Proc Natl Acad Sci USA, 8610029-1003 (1989).

Burdick, D., et al., "Assembly and aggregation properties of synthetic Alzheimer's A4/β amyloid peptide analogs," J Biol Chem, 267:546-55 (1992).

Co, M.S., et al., "Chimeric and humanized antibodies with specificity for the CD33 antigen," J Immunol, 148:1149-1154 (1992).

Ghersi-Egea, et al., "Fate of Cerebrospinal Fluid-Borne Amyloid β-Peptide: Rapid Clearance into Blood and Appreciable Accumulation by Cerebral Arteries," Journal of Neurochemistry, vol. 67(2), 880-883 (1996).

Kawarabayashi, et al., "Age-Dependent Changes in Brain, CSF, and Plasma Amyloid β Protein in the Tg2576 Transgenic Mouse Model of Alzheimer's Disease," J. Neuroscience, 21:372-381 (2001).

Paul, W.E., Fundamental Immunology, 3rd edition, 1993, pp. 292-295.

Rudikoff, et al., Single amino acid substitution altering antigen-binding specificity. Proc. Natl Acad. Sci. USA Mar. 1982; 79(6):1979-83.

Aβ BINDING MOLECULES

This application is a continuation of U.S. patent application Ser. No. 12/504,818 filed on Jul. 17, 2009, which claims the priority of U.S. patent application Ser. 10/544,050, filed on Feb. 6, 2004, which is U.S. Pat. No. 7,575,747, granted on Aug. 18, 2009, which claims the priority of PCT application PCT/US2004/034970 filed on Feb. 6, 2004, which claims the priority of U.S. provisional application No. 60/446,380 filed Feb. 10, 2003.

BACKGROUND OF THE INVENTION

The invention relates to humanized antibodies that bind to the amyloid beta peptide (Aβ) and to preventative and therapeutic treatment of conditions associated with the Aβ peptide, such as Alzheimer's disease, Down's syndrome, and cerebral amyloid angiopathy.

The Aβ peptide in circulating form is composed of 39-43 amino acids (mostly 40 or 42 amino acids) resulting from the cleavage of a precursor protein, amyloid precursor protein (APP). Conversion of Aβ from soluble to insoluble forms with high β-sheet content and its deposition as neuritic and cerebrovascular plaques in the brain appears to be associated with a number of conditions and diseases. Among these conditions and diseases are both pre-clinical and clinical Alzheimer's disease, Down's syndrome, and pre-clinical and clinical cerebral amyloid angiopathy (CAA). Prevention and/or reversal of Aβ deposition are promising methods for treating conditions associated with the Aβ peptide.

Therapeutic agents which may prevent or reverse Aβ deposition include antibodies to Aβ peptide. WO 00/72880 and Bard, F., et al., Nature Med. (2000) 6:916-919 describe significant reduction in plaque in cortex and hippocampus in a transgenic mouse model of Alzheimer's disease when treated using N-terminal fragments of Aβ peptides and antibodies that bind to them, but not when treated with the Aβ 13-28 fragment conjugated to sheep anti-mouse IgG or with an antibody against the 13-28 fragment, antibody 266. N-terminal directed antibodies were asserted to cross the blood-brain barrier and to induce phagocytosis of amyloid plaques based on in vitro studies as well as a subsequent, ex vivo assay (Bard, F. et al., Proc. Natl. Acad. Sci. (2003) 100:2023-2028).

U.S. Pat. Nos. 5,766,846; 5,837,672; and 5,593,846 (which are incorporated herein by reference) describe the production of murine monoclonal antibodies to the central domain of the Aβ peptide. Among antibodies known to bind between amino acids 13 and 28 of Aβ are mouse antibodies 266, 4G8, and 1C2.

It had been previously been found, as described in WO 01/62801, that administration of the mouse antibody 266 (m266) almost completely restores cognition following prolonged periods of weekly administration of the 266 antibody (object memory) in 24-month old hemizygous transgenic mice (APP$^{V717F}$). It was also observed that peripheral administration of antibody 266 results in rapid efflux of relatively large quantities of Aβ peptide from the CNS into the plasma. Prolonged treatment also resulted in altered clearance of soluble Aβ, prevention of plaque formation, and improvement in cognition, even without necessarily having the features the art teaches are required for an antibody to be effective, namely, reducing Aβ amyloid plaque burden, crossing the blood brain barrier to any significant extent, decorating plaque, activating cellular mechanisms, or binding with great affinity to aggregated Aβ.

In conjunction with disclosing results with a mouse model indicating a therapeutic utility of a 266 antibody, WO 01/62801 also disclosed humanized 266 antibodies. These antibodies contain variations in framework regions surrounding complementary determining regions (CDRs) of antibody m266, as well as two amino acid substitutions at a single position in CDR1 of the m266 light chain. Additional humanized 266 antibodies are disclosed in PCT/US02/21322, in which amino acid substitutions occur at three positions in CDR2 from the heavy chain of antibody m266.

Therapeutically beneficial antibodies that bind to the epitope recognized by m266 will desirably be stable in solution, display favorable pharmacokinetics, and possess affinity toward an epitope formed by amino acids 13 and 28 of Aβ. Thus, there is a need in the art for additional antibodies possessing characteristics similar to or better than m266 which will be efficacious in humans.

SUMMARY OF THE INVENTION

This invention provides an antibody or fragment thereof that binds Aβ in which the antibody has a light chain and a heavy chain, such that the light chain has a light chain complementary determining region (CDR) 1 that is either SEQ ID NO:7, 8, 9, 10, 11, 12, 13, 14, 15, 16, 17, 18, 18, 20, 21, or 22, a light chain CDR2 that is either SEQ ID NO:23, 24, 25, 26 or 27, and a light chain CDR3 that is either SEQ ID NO:28, 29, 30, 31, 32, 33, 34, 35, or 36, and wherein the heavy chain has a heavy chain CDR1 that is either SEQ ID NO:37 or 38, a heavy chain CDR2 that is either SEQ ID NO:39, 40, 41, 42, 43, 44, 45, 46, 47, 48, 49, 50, 51, 52, 53, 54, 55, 56, 57, 58, 59, 60 , 61, 62, 63, 64, 65, 66, 67 or 68, and a heavy chain CDR3 that is either SEQ ID NO:69, 70, 71, 72, 73, 74, 75, or 76, provided that no antibody has a light chain CDR1 of SEQ ID NO:7; a light chain CDR2 of SEQ ID NO:23, a light chain CDR3 of SEQ ID NO:28, a heavy chain CDR1 of SEQ ID NO:37, a heavy chain CDR2 of SEQ ID NO:39, and a heavy chain CDR3 of SEQ ID NO:69.

The invention also includes methods of treating, preventing, or reversing conditions and diseases associated with Aβ peptide, including both pre-clinical and clinical Alzheimer's disease, Down's syndrome, and pre-clinical and clinical cerebral amyloid angiopathy (CAA). These methods comprise administering to a subject an effective amount of an antibody described and claimed herein.

DETAILED DESCRIPTION OF THE INVENTION

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Based on this ordering, the CDRs of the light chain may be referred to as CDR L1, CDR L2, and CDR L3, while the CDRs of the heavy chain may be referred to as CDR H1, CDR H2, and CDR H3. The assignment of amino acids to each domain is in accordance with well known conventions [Kabat "Sequences of Proteins of Immunological Interest," National Institutes of Health, Bethesda, Md., 1987 and 1991; Chothia et al. J. Mol. Biol. (1987) 196:901-917; Chothia, et al., Nature (1989) 342:878-883]. The CDRs include residues defined by Kabat and Chothia (underlined in the m266 sequence). Light chains are classified as kappa and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 3 or more amino acids.

IgG antibodies are the most abundant immunoglobulin in serum. IgG also has the longest half-life in serum of any immunoglobulin. Unlike other immunoglobulins, IgG is efficiently recirculated following binding to FcR. There are four IgG subclasses G1, G2, G3, and G4, each of which have different effector functions. G1, G2, and G3 can bind C1q and fix complement while G4 cannot. Even though G3 is able to bind C1q more efficiently than G1, G1 is more effective at mediating complement-directed cell lysis. G2 fixes complement very inefficiently. The C1q binding site in IgG is located at the carboxy terminal region of the CH2 domain.

All IgG subclasses are capable of binding to Fc receptors (CD16, CD32, CD64) with G1 and G3 being more effective than G2 and G4. The Fc receptor binding region of IgG is formed by residues located in both the hinge and the carboxy terminal regions of the CH2 domain.

The term "fragment" of an antibody as used herein refers to one or more fragments of an antibody that retain the ability to bind to an antigen (e.g., Aβ.). It has been shown that the antigen-binding function of an antibody can be performed by fragments of a full-length antibody. Examples of binding fragments encompassed within the term "fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, and (v) a dAb fragment (Ward et al., (1989) Nature 341:544-546), which consists of a VH domain. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426: and Huston et al. (1988) Proc. Natl. Acad. Sci. USA 85:5879-5883). Such single chain antibodies are also intended to be encompassed within the term "fragment" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

Still further, an antibody or fragment thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody fragments, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as are well known in the art.

The term "humanized antibody" refers to an antibody that is composed partially or fully of amino acid sequences derived from a human antibody germline or a rearranged sequence and made by altering the sequence of an antibody having non-human complementarity determining regions (CDRs). The framework regions of the variable regions are substituted by corresponding human framework regions. The human framework regions include genomic framework regions, as well as those containing one or more amino acid substitutions. In particular, such substitutions include mutations in which an amino acid at a particular position in the human framework is replaced with the amino acid from the corresponding position of the natural framework for the non-human CDR. For example, a humanized antibody having mouse CDRs may contain one or more substitutions that replace a particular human framework amino acid with the corresponding mouse framework amino acid. As discussed herein, antibody in the context of humanized antibody is not limited to a full-length antibody and can include fragments and single chain forms.

The antibodies of the present invention are monoclonal antibodies. Such antibodies, however, are monoclonal only in the sense that they may be derived from a clone of a single cell type. However, this is not meant to limit them to a particular origin. Such antibodies may be readily produced in cells that commonly do not produce antibodies, such as CHO, NSO, or COS cells. In addition, such antibodies may be produced in other types of cells, especially mammalian and even plant cells, by genetically engineering such cells to express and assemble the polypeptide light and heavy chains forming the antibody product. In addition, such chains can be chemically synthesized but, since they would be specific for a given antigenic determinant, would still constitute "monoclonal" antibodies within the spirit in which that term is used. Thus, as used herein, the term monoclonal antibody is intended to denote more the specificity and purity of the antibody molecules rather than the mere mechanism used for production of said antibodies.

The term "$K_D$", as used herein, is intended to refer to the dissociation constant of a particular antibody-antigen interaction. It is calculated by the formula:

$$K_D = k_{off}/k_{on} \text{ (measured in } M\text{)}$$

The term "$k_{on}$" as used herein is intended to refer to the association rate constant, or specific reaction rate, of the forward, or complex-forming, reaction, measured in units: $M^{-1} \sec^{-1}$. The term "$k_{off}$", as used herein, is intended to refer to the dissociation rate constant, or specific reaction rate, for dissociation of an antibody from the antibody/antigen complex, measured in units: $\sec^{-1}$.

The term "nucleic acid molecule", as used herein, is intended to include DNA molecules and RNA molecules. A nucleic acid molecule may be single-stranded or double-stranded, but preferably is double-stranded DNA.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operably linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The light and heavy chains of m266 have the following sequences:

m266 light chain:
(SEQ ID NO: 1)
DVVMTQTPLSLPVSLGDQASISC<u>RSSQSLIYSDGNAYLH</u>WFLQKPGQSPK LLIY<u>KVS</u>

<u>NRFS</u>GVPDRFSGSGSGTDFTLKISRVETEDLGVYFC<u>SQSTHVPWT</u>FGGGT

KLEIK.

m266 heavy chain:
(SEQ ID NO: 2)
EVKLVESGGGLVQPGGSLKLSCAVS<u>GFTFSRYSMS</u>WVRQTPEKRLELVAQ <u>INSVGNSTYYPDTVKG</u>RFTISRDNAEYTLSLQMSGLRSDDTATYYCAS<u>GD</u>

<u>YW</u>GQGTTLTVSS

The CDRs include residues defined by Kabat and Chothia. The underlined portions represent the sequences that have been identified as the m266 CDRs, which are listed in Table 1.

TABLE 1 m266 CDR sequences

| CDR | Sequence | SEQ ID NO: |
|---|---|---|
| L1 | RSSQSLIYSDGNAYLH | 7 |
| L2 | KVSNRFS | 23 |

TABLE 1-continued m266 CDR sequences

| CDR | Sequence | SEQ ID NO: |
|---|---|---|
| L3 | SQSTHVPWT | 28 |
| H1 | GFTFSRYSMS | 37 |
| H2 | QINSVGNSTYYPDTVKG | 39 |
| H3 | GDY | 69 |

The antibodies of the present invention include humanized antibodies, in which CDR sequences corresponding to or derived from those of m266 are effectively grafted into a human antibody framework. An important aspect of humanizing antibodies from another species is to reduce the possibility that the antibody causes an immune response when injected into a human patient as a therapeutic. The more sequences that are employed in a humanized antibody resemble those of human antibodies, the lower the risk of immunogenicity. In addition, the injected humanized antibodies generally have a longer half-life in the circulation than injected non-human antibodies. Furthermore, if effector function is desired, because the effector portion is human, it may interact better with the other parts of the human immune system.

In principle, a framework sequence from any human antibody may serve as the template for CDR grafting. However, the framework context of CDRs influences their binding to antigen, such that variation between different frameworks may lead to some or significant loss of binding affinity to the antigen.

Preferred human framework amino acid sequences for the light chain variable region of the antibodies of the present invention include the following sequences, which for illustrative purposes are represented with the CDRs of m266 (underlined sequences) inserted:

(SEQ ID NO: 3)
DIVMTQTPLSLSVTPGQPASISC <u>RSSQSLIYSDGNAYLH</u>

WYLQKPGQSPQLLIY <u>KVSNRFS</u>

GVPDRFSGSGSGTDFTLKISRVEAEDVGVYYC <u>SQSTHVPWT</u>

FGGGTKVEIK;

(SEQ ID NO: 4)
DVVMTQSPLSLPVTLGQPASISC <u>RSSQSLIYSDGNAYLH</u>

WFQQRPGQSPRRLIY <u>KVSNRFS</u>

GVPDRFSGSGSGTDFTLKISRVEAEDVGVYYC <u>SQSTHVPWT</u>

FGGGTKVEIK.

Preferred human framework amino acid sequences for the heavy chain variable region of the antibodies of the present invention include the following sequences, which for illustrative purposes are represented with the CDRs of m266 (underlined sequences) inserted:

(SEQ ID NO: 5)
EVQLVESGGGLVKPGGSLRLSCAAS <u>GFTFSRYSMS</u>

WVRQAPGKGLEWVG <u>QINSVGNSTYYPDTVKG</u>

```
                                               -continued
         RFTISRDDSKNTLYLQMNSLKTEDTAVYYCTT GDY

WGQGTLVTVSS;

(SEQ ID NO: 6)
         EVQLLESGGGLVQPGGSLRLSCAAS GFTFSRYSMS

WVRQAPGKGLEWVS QINSVGNSTYYPDTVKG

RFTISRDNSKNTLYLQMNSLRSEDTAVYYCAK GDY

WGQGTLVTVSS.
```

In preferred embodiments, antibodies of the present invention will have a light chain framework as shown in SEQ ID NO:3, and a heavy chain framework as shown in SEQ ID NO:5. In alternative embodiments, antibodies of the present invention will have a light chain framework as shown in SEQ ID NO:4, and a heavy chain framework as shown in SEQ ID NO:6.

Peripheral administration of m266 to a transgenic mouse model of Alzheimer's disease ($APP^{V717F}$ mice) results in a rapid increase in plasma Aβ, indicating that circulating m266 is able to alter the equilibrium of Aβ between CNS and plasma, yielding a net increase in Aβ efflux from CNS and a net decrease of Aβ efflux into CNS (WO 01/62801; DeMattos et al., *Proc. Natl. Acad. Sci.* 98:8850-8855 (2001)). Preferably, upon peripheral administration, the antibodies or fragments thereof of the present invention are capable of facilitating Aβ efflux from the central nervous system (CNS) to plasma. The antibodies disclosed herein preferably will facilitate Aβ efflux from CNS into plasma in humans in a manner that is comparable to or, more preferably, more efficient than that through which m266 facilitates Aβ efflux from CNS into plasma in mice.

The antibodies of the present invention or fragments thereof contain light chain and heavy chains having CDRs with amino acids selected from the group consisting of SEQ ID NOS:7, 8, 9, 10, 11, 12, 13, 14, 15, 16, 17, 18, 18, 20, 21, and 22 for CDR L1, SEQ ID NOS:23, 24, 25, 26 and 27 for CDR L2, SEQ ID NOS:28, 29, 30, 31, 32, 33, 34, 35, and 36 for CDR L3, SEQ ID NOS:37 and 38 for CDR H1, SEQ ID NOS:39, 40, 41, 42, 43, 44, 45, 46, 47, 48, 49, 50, 51, 52, 53, 54, 55, 56, 57, 58, 59, 60 , 61, 62, 63, 64, 65, 66, 67 and 68 for CDR H2, and SEQ ID NOS:69, 70, 71, 72, 73, 74, 75, and 76 for CDR H3, provided that no antibody has the combination of SEQ ID NO:7 for CDR L1, SEQ ID NO:23 for CDR L2, SEQ ID NO:28 for CDR L3, SEQ ID NO:37 for CDR H1, SEQ ID NO:39 for CDR H2, and SEQ ID NO:69 for CDR H3.

CDR H2 of antibody m266 is glycosylated due to its Asn-Ser-Thr sequence, as described in PCT/US02/21322. This sequence is an example of an Asn-X-Ser/Thr signal for N-linked glycosylation, wherein the Asn is the site of attachment of N-linked glycosyl chains. Removal of the CDR H2 glycosylation site in antibodies derived from m266 advantageously provides for more reliable antibody production and less batch-to-batch variability in glycosylation while preserving or improving affinity and specificity. In a preferred embodiment, antibodies of the present invention lacking an N-glycosylation site in CDR H2 contain a light chain and a heavy chain having CDR sequences selected from the following: SEQ ID NO:8 for CDR L1, SEQ ID NOS:23 and 24 for CDR L2, SEQ ID NO:34 for CDR L3, SEQ ID NO:38 for CDR H1, SEQ ID NOS:58, 62, 63, 64, 65, 66, 67, and 68 for CDR H2, and SEQ ID NO:71 for CDR H3.

The antibodies of the present invention contain six CDRs, three from the light chain and three from the heavy chain. A given antibody may contain 1, 2, 3, 4, or up to 5 CDRs which are identical to the corresponding CDRs from m266, with the remaining 5, 4, 3, 2, or 1 CDR(s) being derived from m266. For example, an antibody of the present invention might contain CDRs L1, L2, L3, H1, and H2 that are identical to m266 CDRs L1, L2, L3, H1 and H2, with CDR H3 being a CDR derived from m266 CDR H3 (as represented by SEQ ID NOS:70, 71, 72, 73, 74, 75, and 76).

The CDRs described herein can be used to make full-length antibodies as well as functional fragments and analogs or other proteins which incorporate the CDRs in an active structural conformation, such that the protein employing the CDRs binds Aβ.

Table 2 indicates the amino acid sequences (using standard amino acid one letter code) of the CDRs employed in the antibodies of the present invention. The CDRs are presented in the table in the context of individual antibody clones (Fab fragments). In Table 2, the locations of amino acid substitutions made relative to the corresponding m266 CDRs listed in Table 1 (i.e. locations at which CDRs differ in amino acids) are indicated in bold and underlined. Each of these clones have the respective light and heavy chain framework sequences of SEQ ID NOS:3 and 5, with the exception of clone A7, which has the respective light and heavy chain framework sequences of SEQ ID NOS:4 and 6.

TABLE 2

CDR sequences of selected antibodies having affinity to Aβ

| Clone | CDR | Sequence | SEQ ID NO: |
|---|---|---|---|
| A7 | L1 | RSSQSLIYSDGNAYLH | 7 |
|  | L2 | KVSNRFS | 23 |
|  | L3 | SQSTHVPWA | 29 |
|  | H1 | GFTFSRYSMS | 37 |
|  | H2 | QISSVGNSTYYPDTVKG | 40 |
|  | H3 | GPY | 70 |
| 1B7 | L1 | RSSQSLIYSDGNAYLH | 7 |
|  | L2 | KVSNRFS | 23 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 1E1 | L1 | RSSQSLIYSDGNAYLH | 7 |
|  | L2 | KVSNRFS | 23 |
|  | L3 | SQSTHSPWT | 30 |
|  | H1 | GFTFSRYSMS | 37 |
|  | H2 | QINSRGNSTYYPDTVKG | 41 |
|  | H3 | GDH | 72 |
| 3D5 | L1 | RSSQSLIYSDGNAYLH | 7 |
|  | L2 | KVSNRFS | 23 |
|  | L3 | SQSTHSPWT | 30 |
|  | H1 | GFTFSRYSMS | 37 |

TABLE 2-continued

CDR sequences of selected antibodies having affinity to Aβ

| Clone | CDR | Sequence | SEQ ID NO: |
|---|---|---|---|
| | H2 | QINSTGNSTYYPDTVKG | 42 |
| | H3 | GDF | 71 |
| 2A9 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINAVGNSTYYPDTVKG | 43 |
| | H3 | GDF | 71 |
| D3 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSIGNSTYYPDTVKG | 44 |
| | H3 | GDW | 73 |
| 1C5 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSVANSTYYPDTVKG | 45 |
| | H3 | GDF | 71 |
| A3 | L1 | RSSQSLIYSDGNAYLH | 7 |
| | L2 | KVSNRFS | 23 |
| | L3 | SQSTHTPWT | 31 |
| | H1 | GFTFSRYSMS | 37 |
| | H2 | QINSSGNSTYYPDTVKG | 46 |
| | H3 | GDF | 71 |
| A4 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSPGNSTYYPDTVKG | 47 |
| | H3 | GDS | 74 |
| 1D4 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSQGNSTYYPDTVKG | 48 |
| | H3 | GDR | 75 |

TABLE 2-continued

CDR sequences of selected antibodies having affinity to Aβ

| Clone | CDR | Sequence | SEQ ID NO: |
|---|---|---|---|
| 3D12 | L1 | RSSQSLIYSDGNAYLH | 7 |
| | L2 | KVSNRFS | 23 |
| | L3 | SQSTHAPWT | 32 |
| | H1 | GFTFSRYSMS | 37 |
| | H2 | QINSPGNSTYYPDTVKG | 47 |
| | H3 | GDF | 71 |
| 3F9 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSRGNSTYYPDTVKG | 41 |
| | H3 | GDV | 76 |
| 5F11 | L1 | RSSQSLIYSDGNAYLH | 7 |
| | L2 | KVSNRFS | 23 |
| | L3 | SQSTHSPWT | 30 |
| | H1 | GYTFSRYSMS | 38 |
| | H2 | QINSRGNSTYYPDTVKG | 41 |
| | H3 | GDF | 71 |
| 2B2 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINIRGNSTYYPDTVKG | 49 |
| | H3 | GDF | 71 |
| 1A2 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSRGNHTYYPDTVKG | 50 |
| | H3 | GDF | 71 |
| 1B1 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSRGNNTYYPDTVKG | 51 |
| | H3 | GDF | 71 |

TABLE 2-continued

CDR sequences of selected antibodies having affinity to Aβ

| Clone | | CDR Sequence | SEQ ID NO: |
|---|---|---|---|
| 2A11 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSRGNRTYYPDTVKG | 52 |
| | H3 | GDF | 71 |
| 6F9 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSRGNSTYYPDPVKG | 53 |
| | H3 | GDF | 71 |
| 3H1 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSVGNSTYYPDKVKG | 54 |
| | H3 | GDF | 71 |
| 3H2 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSVGNSTYYPDAVKG | 55 |
| | H3 | GDF | 71 |
| 6H8 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSVGNSTYYPDEVKG | 56 |
| | H3 | GDF | 71 |
| 6F6 | L1 | RSSQSLIYSDGNAYLH | 7 |
| | L2 | KVSNRFS | 23 |
| | L3 | SQSTHSPWT | 30 |
| | H1 | GFTFSRYSMS | 37 |
| | H2 | QINSVGNSTYYPDTVTG | 57 |
| | H3 | GDF | 71 |
| 7E1 | L1 | SSSQSLIYSDGNAYLH | 8 |
| | L2 | KVSNRFS | 23 |
| | L3 | SQSTHSPWT | 30 |
| | H1 | GFTFSRYSMS | 37 |
| | H2 | QINSRGNSTYYPDTVKG | 41 |
| | H3 | GDF | 71 |
| 4D1 | L1 | LSSQSLIYSDGNAYLH | 14 |
| | L2 | KVSNRFS | 23 |
| | L3 | SQSTHSPWT | 30 |
| | H1 | GFTFSRYSMS | 37 |
| | H2 | QINSRGNSTYYPDTVKG | 41 |
| | H3 | GDF | 71 |
| 4D3 | L1 | RVSQSLIYSDGNAYLH | 15 |
| | L2 | KVSNRFS | 23 |
| | L3 | SQSTHSPWT | 30 |
| | H1 | GFTFSRYSMS | 37 |
| | H2 | QINSRGNSTYYPDTVKG | 41 |
| | H3 | GDF | 71 |
| 4D6 | L1 | RSNQSLIYSDGNAYLH | 16 |
| | L2 | KVSNRFS | 23 |
| | L3 | SQSTHSPWT | 30 |
| | H1 | GFTFSRYSMS | 37 |
| | H2 | QINSRGNSTYYPDTVKG | 41 |
| | H3 | GDF | 71 |
| 4D9 | L1 | RSSISLIYSDGNAYLH | 17 |
| | L2 | KVSNRFS | 23 |
| | L3 | SQSTHSPWT | 30 |
| | H1 | GFTFSRYSMS | 37 |
| | H2 | QINSRGNSTYYPDTVKG | 41 |
| | H3 | GDF | 71 |
| 4F12 | L1 | RSSKSLIYSDGNAYLH | 18 |
| | L2 | KVSNRFS | 23 |
| | L3 | SQSTHSPWT | 30 |
| | H1 | GFTFSRYSMS | 37 |
| | H2 | QINSRGNSTYYPDTVKG | 41 |
| | H3 | GDF | 71 |

TABLE 2-continued

CDR sequences of selected antibodies having affinity to Aβ

| Clone | CDR | Sequence | SEQ ID NO: |
|---|---|---|---|
| 4C11 | L1 | RSSQSLIFSDGNAYLH | 19 |
|  | L2 | KVSNRFS | 23 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 6D4 | L1 | RSSQSLIYWDGNAYLH | 9 |
|  | L2 | KVSNRFS | 23 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 6D3 | L1 | RSSQSLIYSDGIAYLH | 10 |
|  | L2 | KVSNRFS | 23 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 6E11 | L1 | RSSQSLIYSDGSAYLH | 11 |
|  | L2 | KVSNRFS | 23 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 6D7 | L1 | RSSQSLIYLDGNAYLH | 12 |
|  | L2 | KVSNRFS | 23 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 3E2 | L1 | RSSQSLIYSDGNNYLH | 20 |
|  | L2 | KVSNRFS | 23 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 3E10 | L1 | RSSQSLIYSDGNHYLH | 21 |
|  | L2 | KVSNRFS | 23 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 3F1 | L1 | RSSQSLIYSDGNAWLH | 22 |
|  | L2 | KVSNRFS | 23 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 5C8 | L1 | RSSQSLIYSDGNAYLH | 7 |
|  | L2 | KVSNRFW | 24 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 5A11 | L1 | RSSQSLIYSDGNAYLH | 7 |
|  | L2 | KVSNRRS | 25 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 5D1 | L1 | RSSQSLIYSDGNAYLH | 7 |
|  | L2 | KVYNRFS | 26 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |
| 5B10 | L1 | RSSQSLIYSDGNAYLH | 7 |
|  | L2 | RVSNRFS | 27 |
|  | L3 | SQSTHSPWT | 30 |
|  | H1 | GFTFSRYSMS | 37 |
|  | H2 | QINSRGNSTYYPDTVKG | 41 |
|  | H3 | GDF | 71 |

TABLE 2-continued

CDR sequences of selected antibodies having affinity to Aβ

| Clone | CDR | Sequence | SEQ ID NO: |
|---|---|---|---|
| 6B6 | L1 | RSSQSLIYSDGNAYLH | 7 |
|  | L2 | KVSNRFS | 23 |
|  | L3 | AQSTHSPWT | 33 |
|  | H1 | GFTFSRYSMS | 37 |
|  | H2 | QINSRGNSTYYPDTVKG | 41 |
|  | H3 | GDF | 71 |
| 6C3 | L1 | RSSQSLIYSDGNAYLH | 7 |
|  | L2 | KVSNRFS | 23 |
|  | L3 | TQSTHSPWT | 34 |
|  | H1 | GFTFSRYSMS | 37 |
|  | H2 | QINSRGNSTYYPDTVKG | 41 |
|  | H3 | GDF | 71 |
| 1E8 | L1 | RSSQSLIYSDGNAYLH | 7 |
|  | L2 | KVSNRFS | 23 |
|  | L3 | SQSTHSPWS | 35 |
|  | H1 | GFTFSRYSMS | 37 |
|  | H2 | QINSRGNSTYYPDTVKG | 41 |
|  | H3 | GDF | 71 |
| 2A6 | L1 | RSSQSLIYSDGNAYLH | 7 |
|  | L2 | KVSNRFS | 23 |
|  | L3 | SQSTHSPWE | 36 |
|  | H1 | GFTFSRYSMS | 37 |
|  | H2 | QINSRGNSTYYPDTVKG | 41 |
|  | H3 | GDF | 71 |
| 1F3 | L1 | SSSQSLIYLDGNAYLH | 13 |
|  | L2 | KVSNRFS | 23 |
|  | L3 | AQSTHSPWT | 33 |
|  | H1 | GYTFSRYSMS | 38 |
|  | H2 | QINIRGNNTYYPDPVKG | 58 |
|  | H3 | GDF | 71 |
| 1A1 | L1 | SSSQSLIYSDGNAYLH | 8 |
|  | L2 | KVSNRFS | 23 |
|  | L3 | TQSTHSPWT | 34 |
|  | H1 | GYTFSRYSMS | 38 |
|  | H2 | QINIRGNNTYYPDTVKG | 59 |
|  | H3 | GDF | 71 |
| 1A7 | L1 | SSSQSLIYLDGNAYLH | 13 |
|  | L2 | KVSNRFS | 23 |
|  | L3 | AQSTHSPWT | 33 |
|  | H1 | GYTFSRYSMS | 38 |
|  | H2 | QINIRGNSTYYPDTVKG | 49 |
|  | H3 | GDF | 71 |
| 11F12 | L1 | RSSQSLIYSDGNAYLH | 7 |
|  | L2 | KVSNRFS | 23 |
|  | L3 | TQSTHSPWT | 34 |
|  | H1 | GYTFSRYSMS | 38 |
|  | H2 | QINIRGNNTYYPDTVKG | 59 |
|  | H3 | GDF | 71 |
| 1F2 | L1 | RSSQSLIYSDGNAYLH | 7 |
|  | L2 | KVSNRFS | 23 |
|  | L3 | TQSTHSPWT | 34 |
|  | H1 | GYTFSRYSMS | 38 |
|  | H2 | QINIRGNSTYYPDPVKG | 60 |
|  | H3 | GDF | 71 |
| 1A12 | L1 | RSSQSLIYSDGNAYLH | 7 |
|  | L2 | KVSNRFS | 23 |
|  | L3 | SQSTHSPWT | 30 |
|  | H1 | GFTFSRYSMS | 37 |
|  | H2 | QINIRGNNTYYPDTVKG | 59 |
|  | H3 | GDF | 71 |
| 1A10 | L1 | SSSQSLIYSDGNAYLH | 8 |
|  | L2 | KVSNRFS | 23 |
|  | L3 | TQSTHSPWT | 34 |
|  | H1 | GYTFSRYSMS | 38 |
|  | H2 | QINIRGNHTYYPDTVKG | 61 |
|  | H3 | GDF | 71 |
| 1B3 | L1 | RSSQSLIYSDGNAYLH | 7 |
|  | L2 | KVSNRFS | 23 |
|  | L3 | AQSTHSPWT | 33 |
|  | H1 | GYTFSRYSMS | 38 |
|  | H2 | QINSRGNNTYYPDTVKG | 51 |
|  | H3 | GDF | 71 |

TABLE 2-continued

CDR sequences of selected antibodies having affinity to Aβ

| Clone | CDR | Sequence | SEQ ID NO: |
|---|---|---|---|
| 1C1 | L1 | SSSQSLIYLDGNAYLH | 13 |
| | L2 | KVSNRFS | 23 |
| | L3 | SQSTHSPWT | 30 |
| | H1 | GYTFSRYSMS | 38 |
| | H2 | QINIRGNNTYYPDTVKG | 59 |
| | H3 | GDF | 71 |
| 1D2 | L1 | SSSQSLIYSDGNAYLH | 8 |
| | L2 | KVSNRFS | 23 |
| | L3 | AQSTHSPWT | 33 |
| | H1 | GYTFSRYSMS | 38 |
| | H2 | QINSRGNNTYYPDTVKG | 51 |
| | H3 | GDF | 71 |
| 1D10 | L1 | RSSQSLIYSDGNAYLH | 7 |
| | L2 | KVSNRFS | 23 |
| | L3 | SQSTHSPWT | 30 |
| | H1 | GYTFSRYSMS | 38 |
| | H2 | QINIRGNNTYYPDTVKG | 59 |
| | H3 | GDF | 71 |
| 7F7 | L1 | SSSQSLIYSDGNAYLH | 8 |
| | L2 | KVSNRFS | 23 |
| | L3 | TQSTHSPWT | 34 |
| | H1 | GYTFSRYSMS | 38 |
| | H2 | QINIRGNNTYYPDPVKG | 58 |
| | H3 | GDF | 71 |
| 1A1W | L1 | SSSQSLIYSDGNAYLH | 8 |
| | L2 | KVSNRFW | 24 |
| | L3 | TQSTHSPWT | 34 |
| | H1 | GYTFSRYSMS | 38 |
| | H2 | QINIRGNNTYYPDTVKG | 59 |
| | H3 | GDF | 71 |
| 1A1-KNT | L1 | SSSQSLIYSDGNAYLH | 8 |
| | L2 | KVSNRFS | 23 |
| | L3 | TQSTHSPWT | 34 |
| | H1 | GYTFSRYSMS | 38 |
| | H2 | QINIRGKNTYYPDTVKG | 62 |
| | H3 | GDF | 71 |
| 1A1-SNL | L1 | SSSQSLIYSDGNAYLH | 8 |
| | L2 | KVSNRFS | 23 |
| | L3 | TQSTHSPWT | 34 |
| | H1 | GYTFSRYSMS | 38 |
| | H2 | QINIRGSNLYYPDTVKG | 63 |
| | H3 | GDF | 71 |
| 1A1-TNS | L1 | SSSQSLIYSDGNAYLH | 8 |
| | L2 | KVSNRFS | 23 |
| | L3 | TQSTHSPWT | 34 |
| | H1 | GYTFSRYSMS | 38 |
| | H2 | QINIRGTNSYYPDTVKG | 64 |
| | H3 | GDF | 71 |
| 1A1-LNT | L1 | SSSQSLIYSDGNAYLH | 8 |
| | L2 | KVSNRFS | 23 |
| | L3 | TQSTHSPWT | 34 |
| | H1 | GYTFSRYSMS | 38 |
| | H2 | QINIRGLNTYYPDTVKG | 65 |
| | H3 | GDF | 71 |
| 1A1-HNT | L1 | SSSQSLIYSDGNAYLH | 8 |
| | L2 | KVSNRFS | 23 |
| | L3 | TQSTHSPWT | 34 |
| | H1 | GYTFSRYSMS | 38 |
| | H2 | QINIRGHNTYYPDTVKG | 66 |
| | H3 | GDF | 71 |
| 1A1W-KNT | L1 | SSSQSLIYSDGNAYLH | 8 |
| | L2 | KVSNRFW | 24 |
| | L3 | TQSTHSPWT | 34 |
| | H1 | GYTFSRYSMS | 38 |
| | H2 | QINIRGKNTYYPDTVKG | 62 |
| | H3 | GDF | 71 |
| 1A1W-KET | L1 | SSSQSLIYSDGNAYLH | 8 |
| | L2 | KVSNRFW | 24 |
| | L3 | TQSTHSPWT | 34 |
| | H1 | GYTFSRYSMS | 38 |
| | H2 | QINIRGKETYYPDTVKG | 67 |
| | H3 | GDF | 71 |

TABLE 2-continued

CDR sequences of selected antibodies having affinity to Aβ

| Clone | | CDR Sequence | SEQ ID NO: |
|---|---|---|---|
| 1A1W-KST | L1 | SSSQSLIYSDGNAYLH | 8 |
| | L2 | KVSNRFW | 24 |
| | L3 | TQSTHSPWT | 34 |
| | H1 | GYTFSRYSMS | 38 |
| | H2 | QINIRGKSTYYPDTVKG | 68 |
| | H3 | GDF | 71 |

Each of the clones listed in Table 2 have been demonstrated to bind to Aβ, as determined by screening assays, including a capture filter lift assay and a capture ELISA. Subsequently, several clones were further characterized for binding properties as described below in the Examples.

The antibodies of the present invention represented by the different clones listed in Table 2 differ from each other by sequence changes in at least 1 CDR, and up to as many as 6 CDRs. The differences in CDRs among the clones is indicative of the interchangeable nature of the CDRs, wherein one CDR L1 may be substituted for another CDR L1, one CDR L2 substituted for another CDR L2, and so forth. Accordingly, the various CDR combinations present in the antibodies of the present invention are anticipated to bind Aβ.

Several of the antibodies of the present invention were obtained through combination of CDR substitutions found in other antibodies. These antibodies include 1F3, 1A1, 1A7, 11F12, 1F2, 1A12, 1A10, 1B3, 1C1, 1D2, 1D10, and 7F7. For example, antibody 1A1 was obtained by combining the mutations found in antibodies 2B2 and 1B1. Theoretically, each of the amino acid substitutions indicated in Table 2 may be combined to yield additional antibodies that are likely to specifically bind to Aβ. Antibodies of the present invention therefore encompass additional CDRs derived through combination of the CDR substitutions listed in Table 2.

CDRs of antibodies of the present invention may also encompass alternative substitutions obtained by conservative amino acid substitution of the specific substitutions indicated in Table 2. "Conservative substitution" or "conservative amino acid substitution" is well known in the art and refers to replacement of one or more amino acid residue(s) in a protein or peptide with an amino acid residue that has a common side chain property. As is known in the art, groupings of amino acids based on side chain properties include, but are not limited to, hydrophobic, neutral hydrophilic, acidic, basic, and aromatic amino acids. For example, an alternative to CDR H2 of antibody 1B7 (see Table 2, clone 1B7) may be obtaining by replacing the basic arginine (R) residue of SEQ ID NO:41 with a lysine (K).

The affinity of a given antibody for Aβ is one of several properties that is likely to contribute to its utility for a particular application of the antibody. In one embodiment, antibodies of the present invention will have an affinity for Aβ equal to or, more preferably, greater than m266, as determined by $K_D$. As described above, $K_D$ is measured by the ratio of the $k_{on}$ and $k_{off}$ constants. For example, a $k_{on}$ of $3.1 \times 10^7$ $(M^{-1} sec^{-1})$ and a $k_{off}$ of $0.9 \times 10^{-4} (sec^{-1})$ would combine to give a $K_D$ of $2.8 \times 10^{-12}$ M. Thus, affinity can be improved by increasing the $k_{on}$ or decreasing the $k_{off}$. Several of the antibodies listed in Table 2 have improved affinity for Aβ, based on determination of $K_D$ or $k_{on}$, as described in Examples 1 and 2.

The antibodies of the invention can be present in a relatively pure or isolated form as well as in a supernatant drawn from cells grown in wells or on plates. The antibodies of the invention can also be present in the form of a composition comprising the antibody of the invention and a pharmacologically acceptable diluent or excipient, in which the antibody is suspended. The antibodies of the invention may be present in such a composition at a concentration, or in an amount, sufficient to be of therapeutic or pharmacological value in treating or preventing diseases (for example, preventing Alzheimer's disease). The antibodies may also be present in a composition in a more dilute form.

In another aspect, the present invention also is directed to recombinant DNA encoding the antibodies and fragments of the invention. The sequence of recombinant DNA encoding an antibody or fragment of the invention can be readily determined by one of skill in the art using the genetic code. A nucleic acid having the determined sequence can be prepared and expressed in any of a wide variety of host systems using techniques that are well known in the art.

Preferably, the DNA encodes antibodies that, when expressed, comprise one to five of the light and heavy chain CDRs of m266 [SEQ ID NOS:7, 23, 28, 37, 39, 69], and one or more of the light and heavy chain CDRs of the present invention [SEQ ID NOS:8-22, 24-27, 29-36, 38, 40-68, 70-76]. In addition, the DNA preferably encodes antibodies that, when expressed, comprise these CDRs in combination with a light chain framework of either SEQ ID NOS:3 or 5, and a heavy chain framework of either SEQ ID NOS:4 or 6. More preferably, the light and heavy chains will consist of either SEQ ID NOS:3 and 5 or SEQ ID NOS:4 and 6.

DNA encoding the antibodies of the present invention will typically further include an expression control polynucleotide sequence operably linked to the antibody coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, the collection and purification of the light chains, heavy chains, light/heavy chain dimers or intact antibodies, binding fragments or other immunoglobulin forms may follow.

The nucleic acid sequences of the present invention capable of ultimately expressing the desired antibodies can be formed from a variety of different polynucleotides (genomic or cDNA, RNA, synthetic oligonucleotides, etc.) and components (e.g., V, J, D, and C regions), using any of a variety of well known techniques. Joining appropriate genomic and synthetic sequences is a common method of production, but cDNA sequences may also be utilized.

Human constant region DNA sequences can be isolated in accordance with well known procedures from a variety of human cells, but preferably from immortalized B-cells. Suitable source cells for the polynucleotide sequences and host cells for immunoglobulin expression and secretion can be obtained from a number of sources well-known in the art.

As described herein, in addition to the antibodies specifically described herein, other "substantially homologous" modified antibodies can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis.

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in vectors using site-directed mutagenesis, such as after CH1 to produce Fab fragments or after the hinge region to produce F(ab')$_2$ fragments. Single chain antibodies may be produced by joining VL and VH with a DNA linker.

The antibodies (including immunologically reactive fragments) are administered to a subject at risk for or exhibiting Aβ-related symptoms or pathology such as clinical or preclinical Alzheimer's disease, Down's syndrome, or clinical or pre-clinical amyloid angiopathy, using standard administration techniques, preferably peripherally (i.e. not by administration into the central nervous system) by intravenous, intraperitoneal, subcutaneous, pulmonary, transdermal, intramuscular, intranasal, buccal, sublingual, or suppository administration. Although the antibodies may be administered directly into the ventricular system, spinal fluid, or brain parenchyma, and techniques for addressing these locations are well known in the art, it is not necessary to utilize these more difficult procedures. The antibodies of the invention are effective when administered by the more simple techniques that rely on the peripheral circulation system. The advantages of the present invention include the ability of the antibody to exert its beneficial effects even though not provided directly to the central nervous system itself. In addition, humanized antibodies used in the invention, when administered peripherally, do not need to elicit a cellular immune response in brain when bound to Aβ peptide or when freely circulating to have their beneficial effects. Further, when administered peripherally they do not need to appreciably bind aggregated Aβ peptide in the brain to have their beneficial effects. Indeed, it has been demonstrated that the amount of antibody that crosses the blood-brain barrier is <0.1% of plasma levels.

The pharmaceutical compositions for administration are designed to be appropriate for the selected mode of administration, and pharmaceutically acceptable excipients such as, buffers, surfactants, preservatives, solubilizing agents, isotonicity agents, stabilizing agents and the like are used as appropriate. Remington's Pharmaceutical Sciences, Mack Publishing Co., Easton Pa., latest edition, incorporated herein by reference, provides a compendium of formulation techniques as are generally known to practitioners.

The concentration of the humanized antibody in formulations from as low as about 0.1% to as much as 15 or 20% by weight and will be selected primarily based on fluid volumes, viscosities, and so forth, in accordance with the particular mode of administration selected. Thus, a pharmaceutical composition for injection could be made up to contain in 1 mL of phosphate buffered saline from 1 to 100 mg of the humanized antibody of the present invention. The formulation could be sterile filtered after making the formulation, or otherwise made microbiologically acceptable. A typical composition for intravenous infusion could have a volume as much as 250 mL of fluid, such as sterile Ringer's solution, and 1-100 mg per mL, or more in antibody concentration. Therapeutic agents of the invention can be frozen or lyophilized for storage and reconstituted in a suitable sterile carrier prior to use. Lyophilization and reconstitution can lead to varying degrees of antibody activity loss (e.g. with conventional immune globulins, IgM antibodies tend to have greater activity loss than IgG antibodies). Dosages may have to be adjusted to compensate. The pH of the formulation will be selected to balance antibody stability (chemical and physical) and comfort to the patient when administered. Generally, pH between 4 and 8 is tolerated.

Although the foregoing methods appear the most convenient and most appropriate for administration of proteins such as humanized antibodies, by suitable adaptation, other techniques for administration, such as transdermal administration and oral administration may be employed provided proper formulation is designed. In addition, it may be desirable to employ controlled release formulations using biodegradable films and matrices, or osmotic mini-pumps, or delivery systems based on dextran beads, alginate, or collagen. In summary, formulations are available for administering the antibodies of the invention and are well-known in the art and may be chosen from a variety of options. Typical dosage levels can be optimized using standard clinical techniques and will be dependent on the mode of administration and the condition of the patient.

In addition to their therapeutic utility, the antibodies of the present invention are useful in diagnosing the amount of brain amyloid burden in patients either at risk for or who have been diagnosed with Alzheimer's disease. In studies with the APP$^{V717F}$ transgenic mouse model of Alzheimer's disease, peripheral administration of mouse m266 resulted in a rapid increase in plasma Aβ (DeMattos et al., *Science* 295:2264-2267 (2002)). The magnitude of this increase was found to highly correlate with amyloid burden in mouse hippocampus and cortex. Peripheral administration of m266 thereby provides a method of quantifying amyloid burden in mice. This method of diagnosing amyloid burden through peripheral administration of antibodies that recognize the same Aβ epitope of m266 may be useful for quantifying brain amyloid burden in patients. Accordingly, the antibodies of the present invention may be used to diagnose the amyloid burden of patients either at risk for or who have been diagnosed with Alzheimer's disease.

The antibodies of the present invention also have useful in vitro applications. For example, the antibodies may be used in determining the presence and levels of Aβ by ELISA, immunocytochemical assays, and the like.

The following examples are intended to illustrate but not to limit the invention.

EXAMPLE 1

Binding Affinity Measurements

Affinities to Aβ of Fab fragments and/or monoclonal antibodies of m266 and preferred antibodies of the present invention were determined by KinExA™ (Sapidyne) measurements. KinExA™ is an instrument that permits the measurement of the kinetics of solution phase binding. (Glass, T. (1995), *Biomedical Products* 20:122-123, Ohmura, N. et al., (2001), *Analytical Chemistry* 73: 3392-3399.)

The Aβ antigen used in these affinity measurements was attached to sepharose beads. Specifically, 0.1 mg of biotinylated β Amyloid peptide 1-40 (Biosource) was bound to 0.5 mL of Avidin Sepharose (Sigma) for 1 hour at room temperature. The beads were then washed three times with 10 mL of phosphate buffered saline pH 7.4 with 0.01% $NaN_3$ (PBSA) and re-suspended in 15 mL of PBSA.

Fabs for these experiments were produced by expression in *E. coli*. Briefly, XL-0 cells were infected with phage harboring the Fab genes for 1 hour at 37° C. The temperature was then lowered to 25° C. and the culture shaken for 16 hours. Fab protein was then extracted form the cells using Bugbuster (Novagen) reagent and purified using nickel beads. (Qiagen).

Monoclonal antibodies used in these experiments were produced by placing DNA encoding the V regions of Fab fragments into a vector encoding the remaining portions of an IgG1 antibody, such that complete IgG1 antibodies would be expressed from the vector. Antibody proteins were expressed by transiently transfecting the IgG1 vectors into 293 EBNA cells. Antibodies were purified using protein A sepharose. Briefly, culture supernatants were loaded onto a 1 ml protein A sepharose column. The column was then washed with 20 ml of PBS and eluted using 0.1M Glycine pH 2.7 and immediately neutralized using 1M Tris pH 9. Antibody containing fractions were then dialyzed into PBS.

For the KinExA™ $K_D$ measurements, twelve two fold serial dilutions of antigen at 2× concentration were prepared in PBSA 0.2% BSA and mixed 1:1 with a 2× antibody sample prepared in the same buffer. Typical 1× concentrations were 10 pM of antibody active sites (0.75 ng/mL) and an upper antigen concentration of 100 pM (0.43 ng/mL). The samples were then allowed to equilibrate for 24-72 hours at room temperature. A KinExA™ instrument (Sapidyne) and standard $K_D$ run file were then used to determine the $K_D$ of the system. Briefly, the KinExA™ flow cell was charged with the β Amyloid peptide coated beads and washed with PBSA. For the first sample, free antibody in solution was captured by the beads washed with PBSA and detected using 1:250 Goat anti-human Cy5 (Jackson Immunochemicals) in PBSA. The flow cell was then flushed, re-charged with beads and the next sample analyzed. The process was repeated until all 12 samples were analyzed. The completed data was analyzed using the KinEXA™ software entering the 1× antigen concentration in each sample to calculate the $K_D$ for the antibody-antigen reaction.

For KinExA™ $k_{on}$ and $k_{off}$ measurements, antigen and antibody were prepared as described above. Antigen and antibody samples at 2× active concentration were prepared in PBSA with 0.2% BSA. Samples were mixed 1:1 and the timing for the experiment started. Typical 1× concentrations were 1 nM antibody active site concentration (75 ng/mL) and 2 nM antigen (8.6 ng/mL). A KinExA™ instrument (Sapidyne) and a kineticsdirect run file were used to follow the reaction. Time for each measurement was determined using the manufacturer's instructions. Free antibody remaining in the reaction was captured using β amyloid coated beads packed into the flow cell washed with PBSA and detected at each time point using 1:250 Goat anti-human Cy5 (Jackson) in PBSA. The flow cell was then flushed and recharged with beads for the next measurement, the process continued until a complete decay curve obtained. The data was analyzed using the KinExA™ Inject software. 1× active concentrations of antibody and antigen and the $K_D$ measured previously were used to calculate the $k_{on}$ and $k_{off}$ for the reaction.

Kinetic parameters of Fab fragments, as determined by KinExA™ following equilibration of Fab fragments with antigen, are provided in Table 3. The kinetic parameters of monoclonal antibodies which were equilibrated with antigen prior to KinExA™ measurement are presented in Table 4.

The $K_D$ determinations from another set of experiments, in which monoclonal antibodies were equilibrated with antigen for either 16 to 24 hours or 48 hours are provided in Table 5.

TABLE 3

Binding properties of anti-Aβ Fab fragments determined by KinExA ™

| Fab Samples | ET* (hours) | $K_D \times 10^{-12}$ M | $k_{on} \times 10^5 M^{-1} sec^{-1}$ | $k_{off} \times 10^{-6} sec^{-1}$ |
|---|---|---|---|---|
| 1A1W | 48 | 0.69 | 17.4 | 1.2 |
| 1A1-KNT* | 48 | 1.0 | 14.2 | 1.4 |
| 1A1 | 24 | 1.9 | 8.3 | 1.6 |
| 11F12 | 24 | 2.7 | 8.7 | 2.4 |
| 1A1-SNL* | 24 | 3.2 | 8.4 | 2.7 |
| 7F7 | 24 | 3.4 | 5.2 | 1.8 |
| 1A12 | 16 | 10.8 | 15.9 | 17.2 |
| m266 | 16 | 137.5 | 3.6 | 49.6 |

*Equilibration time

TABLE 4

Binding properties of anti-Aβ monoclonal antibodies determined by KinExA ™

| Mab Samples | ET* (hours) | $K_D \times 10^{-12}$ M | $k_{on} \times 10^5 M^{-1} sec^{-1}$ | $k_{off} \times 10^{-6} sec^{-1}$ |
|---|---|---|---|---|
| 1A1 | 24 | 1.2 | 8.8 | 1.1 |
| 6C3 | 16 | 7.9 | 12.8 | 10.1 |
| m266 | 16 | 76.5 | 0.88 | 6.73 |
| 1B7 | 16 | 122 | 17.6 | 214.1 |
| 1C5 | 16 | 973 | 4.2 | 371.0 |
| 1D4 | 16 | 6314 | 1.2 | 740.0 |

*Equilibration time

TABLE 5

Affinity for anti-Aβ monoclonal variants measured by KinExA ™

| SAMPLE | $K_D$ (pM) | Fold increase in affinity |
|---|---|---|
| m266 | 67.5 | |
|  | 85.4 | |
|  | 76.5 | 1 |
| 1A1 | 3.2 | |
|  | 5.7 | |
|  | 4.5 | 17 |
| 1A1-W | 2.2 | |
|  | 1.9 | |
|  | 2.1 | 36 |
| 1A1-W[b] | 1.2 | 64 |
| 1A1-KNT[b] | 0.29 | 264 |
| 1B7 | 674 | 0.11 |
| 1D4 | 15100 | 0.005 |

[a]Numbers in bold are the averages calculated from individual experiments and were used to calculate fold increase in affinity.
[b]The samples were equilibrated for 48 hrs before measurements were done.

Example 2

Association Rate Measurements

The kinetics of association of m266 and preferred monoclonal antibodies of the present invention with Aβ were determined using either BIAcore™ or KinExA™ (Sapidyne) measurements.

BIAcore™ is an automated biosensor system that measures molecular interactions (Karlsson, et al. (1991) *J. Immunol. Methods* 145: 229-240). BIAcore™ analyses described herein were carried out at 25° C. In these experiments, antibody was immobilized at low density on a BIAcore™ CM5 or B1 chip. For the m266 antibody, goat anti-mouse Fc (Jackson Immunoresearch) immobilized on CM5 in flow cell 2 was used for measuring binding constants. Goat anti-mouse was used as control antibody in flow cell 1. For the humanized antibodies, protein A or protein A/G was immobilized via amine coupling to flow cells 1 and 2 of a B1 or CM5 sensor chip.

Antibody was then captured only to flow cell 2 at desired levels (usually a 10-60 second injection of antibody) and allowed to stabilize for 5 minutes. For these experiments, a fresh aliquot of Aβ1-40 was thawed and then diluted 1:10 in HBS-EP running buffer. The 1:10 dilution was used to make up a 200 nM Aβ solution which was serially diluted (1:2 dilutions) to a lowest concentration of 6.25 nM. Each concentration was injected over the surface for 5 minutes at a flow rate of 50 µl/min (250 µl total). The Aβ and antibody were eluted from both flow cells with a 40s injection of glycine pH 1.5. The signal is allowed to stabilize for 2 minutes before the next cycle. The data from flow cell 1 is subtracted from flow cell 2 to account for any bulk shifts due to buffer differences or non-specific binding to the sensor chip or Protein A. The various concentrations were injected randomly and each concentration was run in duplicate. Two control runs of buffer only were used to control for any dissociation of antibody from the capture surface. The data was analyzed using the Biaevalution™ software. A 1:1 model with mass transfer and a local Rmax was used as the best fit for the data.

Association rate constants ($k_{on}$) were determined by BIAcore™ for separate preparations of antibodies. The results of these determinations are summarized in Table 6.

Association rate constants ($k_{on}$) of m266 and antibodies of the present invention with Aβ were determined by KinExA™, using methods as described above in Example 1. The results of two separate $k_{on}$ determinations by KinExA™, in which separate preparations of antibodies were used, are provided in Tables 7 and 8. Furthermore, separate preparations of antibodies and Aβ antigen were used for the determinations provided in Table 8.

TABLE 6

Summary of on-rate constants for anti-Aβ monoclonal variants using BIAcore ™

| Sample | $k_{on}$ ($M^{-1}sec^{-1}$ $10^5$) | Fold Increase |
|---|---|---|
| m266 | 1.3 | 1 |
| 1A1 | 3.9 ± 0.3 | 3 |
| 1A1-W | 6.1 ± 0.03 | 5 |
| 1B7 | 5.9 ± 0.3 | 5 |
| 1D4 | 4.7 ± 1 | 4 |
| 1A1-KNT | 4.7 | 4 |
| 1A1-SNL | 4.2 | 3 |
| 1A1-SNL | 4.7 | 4 |
| 1A1-KNT | 4.1 | 3 |
| 1A1-W | 4.1 ± 0.1 | 3 |
| 1A1-W-KNT | 4.2 | 3 |
| 6C3 | 6.1 | 5 |

TABLE 6-continued

Summary of on-rate constants for anti-Aβ monoclonal variants using BIAcore ™

| Sample | $k_{on}$ ($M^{-1}sec^{-1}$ $10^5$) | Fold Increase |
|---|---|---|
| 1A12 | 4.1 | 3 |
| 7F7 | 3.5 | 3 |

Concentrations of human Aβ (1-40) from 200 nM to 1.6 nM in 2-fold serial dilution were used to obtain on-rate constant. The upper half of Table 6 represents determinations made with a first set of antibody preparations, while the lower half represents determinations made with a second set of antibody preparations

TABLE 7

Summary of on-rate constants for anti-Aβ monoclonal variants using KinExA ™

| SAMPLE | $k_{on}$ (×$10^5$ $M^{-1}sec^{-1}$) | Fold increase in $k_{on}$ |
|---|---|---|
| m266 | 2.1 | |
| | 2.4 | |
| | 2.3 | 1 |
| 1A1 | 5.8 | |
| | 5.5 | |
| | 3.9 | |
| | 5.1 | 2 |
| 1A1-W | 14.7 | |
| | 20.8 | |
| | 17.8 | 8 |
| 1B7 | 6.3 | 3 |
| 1A1-KNT | 14 | 6 |
| 1A1-SNL | 11 | 5 |

[a]Numbers in bold are the averages calculated from individual experiments and were used to calculate fold increase in on-rate.

TABLE 8

Summary of on-rate constants for anti-Aβ monoclonal variants using KinExA ™

| SAMPLE | $k_{on}$ (×$10^5$ $M^{-1}sec^{-1}$) |
|---|---|
| m266 | 1.29 |
| | 1.27 |
| | 0.88 |
| | 1.86[b] |
| | 2.40[b,c] |
| | 1.57[c] |
| | 1.54 |
| 1A1 | 10.55 |
| | 9.54 |
| | 9.12 |
| | 8.83 |
| | 8.51[b,c] |
| | 7.62[b] |
| | 9.76[c] |
| | 9.13 |
| 1A1-W | 18.05 |
| 1A1-KNT | 32.26 |
| 1A1-WKNT | 38.31 |

[a]Numbers in bold are the averages calculated from individual experiments.
[b]A separate preparation of antibodies was used for these experiments.
[c]A separate preparation of antigen was used for these experiments.

We claim:

1. An antibody, or antigen-binding portion thereof, that binds human Aβ, comprising a light chain and a heavy chain, wherein the light chain comprises:
   a) the CDR1 of SEQ ID NO:7
   b) the CDR2 of SEQ ID NO:23
   c) the CDR3 of SEQ ID NO:30; and
the heavy chain comprises:
   a) the CDR1 of SEQ ID NO:37
   b) the CDR2 of SEQ ID NO:41
   c) the CDR3 of SEQ ID NO:71.

2. The antibody or antigen-binding portion of claim 1 which is a humanized antibody.

3. The antigen-binding portion of claim 1 which is a Fab fragment.

4. The antigen-binding portion of claim 1 which is a F(ab')2 fragment.

5. The antibody or antigen-binding portion of claim 1, wherein said antibody or antigen-binding portion thereof has an IgG isotype selected from the group consisting of heavy chain constant regions IgG1 and IgG4.

6. A pharmaceutical composition comprising the antibody or antigen-binding portion thereof of claim 1.

7. A method of treating Alzheimer's disease comprising administering to a subject in need thereof of an effective amount of the antibody or antigen-binding portion thereof of claim 1.

8. A method of diagnosing Alzheimer's disease comprising administering to a subject having brain amyloids a diagnostic amount of the antibody or antigen-binding portion thereof of claim 1.

9. An antibody, or antigen-binding portion thereof, that binds human Aβ, comprising a light chain and a heavy chain, wherein the light chain comprises:
   a) the CDR1 of SEQ ID NO:7
   b) the CDR2 of SEQ ID NO:23
   c) the CDR3 of SEQ ID NO:30; and
the heavy chain comprises:
   a) the CDR1 of SEQ ID NO:37
   b) the CDR2 of SEQ ID NO:48
   c) the CDR3 of SEQ ID NO:75.

10. The antibody or antigen-binding of claim 9 which is a humanized antibody.

11. The antigen-binding portion of claim 9 which is a Fab fragment.

12. The antigen-binding portion of claim 9 which is a F(ab')2 fragment.

13. The antibody or antigen-binding portion of claim 9, wherein said antibody or antigen-binding portion thereof has and IgG isotype selected from the group consisting of heavy chain constant regions IgG1 and IgG4.

14. A pharmaceutical composition comprising the antibody or antigen-binding portion thereof of claim 9.

15. A method of treating Alzheimer's disease comprising administering to a subject in need thereof an effective amount of the antibody or antigen-binding portion thereof of claim 9.

16. A method of diagnosing Alzheimer's disease comprising administering to a subject having brain amyloids a diagnostic amount of the antibody or antigen-binding portion thereof of claim 9.

* * * * *

UNITED STATES PATENT AND TRADEMARK OFFICE
CERTIFICATE OF CORRECTION

PATENT NO. : 8,623,365 B2  
APPLICATION NO. : 13/332753  
DATED : January 7, 2014  
INVENTOR(S) : Julian Davies, Ying Tang and Jeffrey Dean Watkins Page 1 of 1

It is certified that error appears in the above-identified patent and that said Letters Patent is hereby corrected as shown below:

On the Title Page, Item (56)

Foreign Patent Documents, column 2, line 19, delete "0221141" and insert -- 02021141 --, therefor;
Foreign Patent Documents, column 2, line 20, delete "0246237" and insert -- 02046237 --, therefor;
Other Publications, page 2, column 1, line 39, delete "epitode" and insert -- epitope --, therefor;
Other Publications, page 2, column 1, line 44, delete "Alzheirner's" and insert -- Alzheimer's --, therefor;
Other Publications, page 2, column 2, line 67, delete "PatholL" and insert -- Pathol --, therefor;
Other Publications, page 3, column 1, line 11, delete "Aβl6-22" and insert -- Aβ16-22 --, therefor;
Other Publications, page 3, column 1, line 36, delete "solubized" and insert -- solubilized --, therefor;
Other Publications, page 3, column 2, line 8, delete "Microhemorrahage" and insert -- Microhemorrhage --, therefor;
Other Publications, page 3, column 2, line 10, delete "Neurosic" and insert -- Neurosci --, therefor;
Other Publications, page 3, column 2, line 18, delete "Deglycoslation" and insert -- Deglycosylation --, therefor;

In the Claims

Column 58, line 20, Claim 13, delete "and" and insert -- an --, therefor.

Signed and Sealed this
Seventh Day of April, 2015

Michelle K. Lee
*Director of the United States Patent and Trademark Office*

SEQUENCE LISTING

<160> NUMBER OF SEQ ID NOS: 78

<210> SEQ ID NO 1
<211> LENGTH: 112
<212> TYPE: PRT
<213> ORGANISM: Mus sp.

<400> SEQUENCE: 1

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 2
<211> LENGTH: 112
<212> TYPE: PRT
<213> ORGANISM: Mus sp.

<400> SEQUENCE: 2

Glu Val Lys Leu Val Glu Ser Gly Gly Gly Leu Val Gln Pro Gly Gly
1               5                   10                  15

Ser Leu Lys Leu Ser Cys Ala Val Ser Gly Phe Thr Phe Ser Arg Tyr
            20                  25                  30

Ser Met Ser Trp Val Arg Gln Thr Pro Glu Lys Arg Leu Glu Leu Val
        35                  40                  45

Ala Gln Ile Asn Ser Val Gly Asn Ser Thr Tyr Tyr Pro Asp Thr Val
    50                  55                  60

Lys Gly Arg Phe Thr Ile Ser Arg Asp Asn Ala Glu Tyr Thr Leu Ser
65                  70                  75                  80

Leu Gln Met Ser Gly Leu Arg Ser Asp Asp Thr Ala Thr Tyr Tyr Cys
                85                  90                  95

Ala Ser Gly Asp Tyr Trp Gly Gln Gly Thr Thr Leu Thr Val Ser Ser
            100                 105                 110

<210> SEQ ID NO 3
<211> LENGTH: 112
<212> TYPE: PRT
<213> ORGANISM: Artificial sequence
<220> FEATURE:
<223> OTHER INFORMATION: light chain

<400> SEQUENCE: 3

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

```
Thr His Val Pro Trp Thr Phe Gly Gly Gly Thr Lys Val Glu Ile Lys
            100                 105                 110

<210> SEQ ID NO 4
<211> LENGTH: 112
<212> TYPE: PRT
<213> ORGANISM: Artificial sequence
<220> FEATURE:
<223> OTHER INFORMATION: heavy chain

<400> SEQUENCE: 4

Asp Val Val Met Thr Gln Ser Pro Leu Ser Leu Pro Val Thr Leu Gly
1               5                   10                  15

Gln Pro Ala Ser Ile Ser Cys Arg Ser Gln Ser Leu Ile Tyr Ser
            20                  25                  30

Asp Gly Asn Ala Tyr Leu His Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
            100                 105                 110

<210> SEQ ID NO 5
<211> LENGTH: 112
<212> TYPE: PRT
<213> ORGANISM: Artificial sequence
<220> FEATURE:
<223> OTHER INFORMATION: light chain

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Trp Val
        35                  40                  45

Gly Gln Ile Asn Ser Val Gly Asn Ser Thr Tyr Tyr Pro Asp Thr Val
    50                  55                  60

Lys Gly Arg Phe Thr Ile Ser Arg Asp Asp Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Gly Asp Tyr Trp Gly Gln Gly Thr Leu Val Thr Val Ser Ser
            100                 105                 110

<210> SEQ ID NO 6
<211> LENGTH: 112
<212> TYPE: PRT
<213> ORGANISM: Artificial sequence
<220> FEATURE:
<223> OTHER INFORMATION: heavy chain

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
```

```
                    20                  25                  30
Ser Met Ser Trp Val Arg Gln Ala Pro Gly Lys Gly Leu Glu Trp Val
            35                  40                  45

Ser Gln Ile Asn Ser Val Gly Asn Ser Thr Tyr Tyr Pro Asp Thr Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Lys Gly Asp Tyr Trp Gly Gln Gly Thr Leu Val Thr Val Ser Ser
            100                 105                 110

<210> SEQ ID NO 7
<211> LENGTH: 16
<212> TYPE: PRT
<213> ORGANISM: Mus sp.

<400> SEQUENCE: 7

Arg Ser Ser Gln Ser Leu Ile Tyr Ser Asp Gly Asn Ala Tyr Leu His
1               5                   10                  15

<210> SEQ ID NO 8
<211> LENGTH: 16
<212> TYPE: PRT
<213> ORGANISM: Artificial sequence
<220> FEATURE:
<223> OTHER INFORMATION: substituted CDR

<400> SEQUENCE: 8

Ser Ser Ser Gln Ser Leu Ile Tyr Ser Asp Gly Asn Ala Tyr Leu His
1               5                   10                  15

<210> SEQ ID NO 9
<211> LENGTH: 16
<212> TYPE: PRT
<213> ORGANISM: Artificial sequence
<220> FEATURE:
<223> OTHER INFORMATION: substituted CDR

<400> SEQUENCE: 9

Arg Ser Ser Gln Ser Leu Ile Tyr Trp Asp Gly Asn Ala Tyr Leu His
1               5                   10                  15

<210> SEQ ID NO 10
<211> LENGTH: 16
<212> TYPE: PRT
<213> ORGANISM: Artificial sequence
<220> FEATURE:
<223> OTHER INFORMATION: substituted CDR

<400> SEQUENCE: 10

Arg Ser Ser Gln Ser Leu Ile Tyr Ser Asp Gly Ile Ala Tyr Leu His
1               5                   10                  15

<210> SEQ ID NO 11
<211> LENGTH: 16
<212> TYPE: PRT
<213> ORGANISM: Artificial sequence
<220> FEATURE:
<223> OTHER INFORMATION: substituted CDR

<400> SEQUENCE: 11

Arg Ser Ser Gln Ser Leu Ile Tyr Ser Asp Gly Ser Ala Tyr Leu His
1               5                   10                  15
```

<210> SEQ ID NO 12
<211> LENGTH: 16
<212> TYPE: PRT
<213> ORGANISM: Artificial sequence
<220> FEATURE:
<223> OTHER INFORMATION: substituted CDR

<400> SEQUENCE: 12

Arg Ser Ser Gln Ser Leu Ile Tyr Leu Asp Gly Asn Ala Tyr Leu His
1               5                   10                  15

<210> SEQ ID NO 13
<211> LENGTH: 16
<212> TYPE: PRT
<213> ORGANISM: Artificial sequence
<220> FEATURE:
<223> OTHER INFORMATION: substituted CDR

<400> SEQUENCE: 13

Ser Ser Ser Gln Ser Leu Ile Tyr Leu Asp Gly Asn Ala Tyr Leu His
1               5                   10                  15

<210> SEQ ID NO 14
<211> LENGTH: 16
<212> TYPE: PRT
<213> ORGANISM: Artificial sequence
<220> FEATURE:
<223> OTHER INFORMATION: substituted CDR

<400> SEQUENCE: 14

Leu Ser Ser Gln Ser Leu Ile Tyr Ser Asp Gly Asn Ala Tyr Leu His
1               5                   10                  15

<210> SEQ ID NO 15
<211> LENGTH: 16
<212> TYPE: PRT
<213> ORGANISM: Artificial sequence
<220> FEATURE:
<223> OTHER INFORMATION: substituted CDR

<400> SEQUENCE: 15

Arg Val Ser Gln Ser Leu Ile Tyr Ser Asp Gly Asn Ala Tyr Leu His
1               5                   10                  15

<210> SEQ ID NO 16
<211> LENGTH: 16
<212> TYPE: PRT
<213> ORGANISM: Artificial sequence
<220> FEATURE:
<223> OTHER INFORMATION: substituted CDR

<400> SEQUENCE: 16

Arg Ser Asn Gln Ser Leu Ile Tyr Ser Asp Gly Asn Ala Tyr Leu His
1               5                   10                  15

<210> SEQ ID NO 17
<211> LENGTH: 16
<212> TYPE: PRT
<213> ORGANISM: Artificial sequence
<220> FEATURE:
<223> OTHER INFORMATION: substituted CDR

<400> SEQUENCE: 17

Arg Ser Ser Ile Ser Leu Ile Tyr Ser Asp Gly Asn Ala Tyr Leu His
1               5                   10                  15

<210> SEQ ID NO 18

```
<211> LENGTH: 16
<212> TYPE: PRT
<213> ORGANISM: Artificial sequence
<220> FEATURE:
<223> OTHER INFORMATION: substituted CDR

<400> SEQUENCE: 18

Arg Ser Ser Lys Ser Leu Ile Tyr Ser Asp Gly Asn Ala Tyr Leu His
1               5                   10                  15

<210> SEQ ID NO 19
<211> LENGTH: 16
<212> TYPE: PRT
<213> ORGANISM: Artificial sequence
<220> FEATURE:
<223> OTHER INFORMATION: substituted CDR

<400> SEQUENCE: 19

Arg Ser Ser Gln Ser Leu Ile Phe Ser Asp Gly Asn Ala Tyr Leu His
1               5                   10                  15

<210> SEQ ID NO 20
<211> LENGTH: 16
<212> TYPE: PRT
<213> ORGANISM: Artificial sequence
<220> FEATURE:
<223> OTHER INFORMATION: substituted CDR

<400> SEQUENCE: 20

Arg Ser Ser Gln Ser Leu Ile Tyr Ser Asp Gly Asn Asn Tyr Leu His
1               5                   10                  15

<210> SEQ ID NO 21
<211> LENGTH: 16
<212> TYPE: PRT
<213> ORGANISM: Artificial sequence
<220> FEATURE:
<223> OTHER INFORMATION: substituted CDR

<400> SEQUENCE: 21

Arg Ser Ser Gln Ser Leu Ile Tyr Ser Asp Gly Asn His Tyr Leu His
1               5                   10                  15

<210> SEQ ID NO 22
<211> LENGTH: 16
<212> TYPE: PRT
<213> ORGANISM: Artificial sequence
<220> FEATURE:
<223> OTHER INFORMATION: substituted CDR

<400> SEQUENCE: 22

Arg Ser Ser Gln Ser Leu Ile Tyr Ser Asp Gly Asn Ala Trp Leu His
1               5                   10                  15

<210> SEQ ID NO 23
<211> LENGTH: 7
<212> TYPE: PRT
<213> ORGANISM: Mus sp.

<400> SEQUENCE: 23

Lys Val Ser Asn Arg Phe Ser
1               5

<210> SEQ ID NO 24
<211> LENGTH: 7
<212> TYPE: PRT
<213> ORGANISM: Artificial sequence
<220> FEATURE:
```

```
<223> OTHER INFORMATION: substituted CDR

<400> SEQUENCE: 24

Lys Val Ser Asn Arg Phe Trp
1               5

<210> SEQ ID NO 25
<211> LENGTH: 7
<212> TYPE: PRT
<213> ORGANISM: Artificial sequence
<220> FEATURE:
<223> OTHER INFORMATION: substituted CDR

<400> SEQUENCE: 25

Lys Val Ser Asn Arg Arg Ser
1               5

<210> SEQ ID NO 26
<211> LENGTH: 7
<212> TYPE: PRT
<213> ORGANISM: Artificial sequence
<220> FEATURE:
<223> OTHER INFORMATION: substituted CDR

<400> SEQUENCE: 26

Lys Val Tyr Asn Arg Phe Ser
1               5

<210> SEQ ID NO 27
<211> LENGTH: 7
<212> TYPE: PRT
<213> ORGANISM: Artificial sequence
<220> FEATURE:
<223> OTHER INFORMATION: substituted CDR

<400> SEQUENCE: 27

Arg Val Ser Asn Arg Phe Ser
1               5

<210> SEQ ID NO 28
<211> LENGTH: 9
<212> TYPE: PRT
<213> ORGANISM: Mus sp.

<400> SEQUENCE: 28

Ser Gln Ser Thr His Val Pro Trp Thr
1               5

<210> SEQ ID NO 29
<211> LENGTH: 9
<212> TYPE: PRT
<213> ORGANISM: Artificial sequence
<220> FEATURE:
<223> OTHER INFORMATION: substituted CDR

<400> SEQUENCE: 29

Ser Gln Ser Thr His Val Pro Trp Ala
1               5

<210> SEQ ID NO 30
<211> LENGTH: 9
<212> TYPE: PRT
<213> ORGANISM: Artificial sequence
<220> FEATURE:
<223> OTHER INFORMATION: substituted CDR

<400> SEQUENCE: 30
```

```
Ser Gln Ser Thr His Ser Pro Trp Thr
1               5

<210> SEQ ID NO 31
<211> LENGTH: 9
<212> TYPE: PRT
<213> ORGANISM: Artificial sequence
<220> FEATURE:
<223> OTHER INFORMATION: substituted CDR

<400> SEQUENCE: 31

Ser Gln Ser Thr His Thr Pro Trp Thr
1               5

<210> SEQ ID NO 32
<211> LENGTH: 9
<212> TYPE: PRT
<213> ORGANISM: Artificial sequence
<220> FEATURE:
<223> OTHER INFORMATION: substituted CDR

<400> SEQUENCE: 32

Ser Gln Ser Thr His Ala Pro Trp Thr
1               5

<210> SEQ ID NO 33
<211> LENGTH: 9
<212> TYPE: PRT
<213> ORGANISM: Artificial sequence
<220> FEATURE:
<223> OTHER INFORMATION: substituted CDR

<400> SEQUENCE: 33

Ala Gln Ser Thr His Ser Pro Trp Thr
1               5

<210> SEQ ID NO 34
<211> LENGTH: 9
<212> TYPE: PRT
<213> ORGANISM: Artificial sequence
<220> FEATURE:
<223> OTHER INFORMATION: substituted CDR

<400> SEQUENCE: 34

Thr Gln Ser Thr His Ser Pro Trp Thr
1               5

<210> SEQ ID NO 35
<211> LENGTH: 9
<212> TYPE: PRT
<213> ORGANISM: Artificial sequence
<220> FEATURE:
<223> OTHER INFORMATION: substituted CDR

<400> SEQUENCE: 35

Ser Gln Ser Thr His Ser Pro Trp Ser
1               5

<210> SEQ ID NO 36
<211> LENGTH: 9
<212> TYPE: PRT
<213> ORGANISM: Artificial sequence
<220> FEATURE:
<223> OTHER INFORMATION: substituted CDR

<400> SEQUENCE: 36

Ser Gln Ser Thr His Ser Pro Trp Glu
1               5
```

```
<210> SEQ ID NO 37
<211> LENGTH: 10
<212> TYPE: PRT
<213> ORGANISM: Mus sp.

<400> SEQUENCE: 37

Gly Phe Thr Phe Ser Arg Tyr Ser Met Ser
1               5                   10

<210> SEQ ID NO 38
<211> LENGTH: 10
<212> TYPE: PRT
<213> ORGANISM: Artificial sequence
<220> FEATURE:
<223> OTHER INFORMATION: substituted CDR

<400> SEQUENCE: 38

Gly Tyr Thr Phe Ser Arg Tyr Ser Met Ser
1               5                   10

<210> SEQ ID NO 39
<211> LENGTH: 17
<212> TYPE: PRT
<213> ORGANISM: Mus sp.

<400> SEQUENCE: 39

Gln Ile Asn Ser Val Gly Asn Ser Thr Tyr Tyr Pro Asp Thr Val Lys
1               5                   10                  15

Gly

<210> SEQ ID NO 40
<211> LENGTH: 17
<212> TYPE: PRT
<213> ORGANISM: Artificial sequence
<220> FEATURE:
<223> OTHER INFORMATION: substituted CDR

<400> SEQUENCE: 40

Gln Ile Ser Ser Val Gly Asn Ser Thr Tyr Tyr Pro Asp Thr Val Lys
1               5                   10                  15

Gly

<210> SEQ ID NO 41
<211> LENGTH: 17
<212> TYPE: PRT
<213> ORGANISM: Artificial sequence
<220> FEATURE:
<223> OTHER INFORMATION: substituted CDR

<400> SEQUENCE: 41

Gln Ile Asn Ser Arg Gly Asn Ser Thr Tyr Tyr Pro Asp Thr Val Lys
1               5                   10                  15

Gly

<210> SEQ ID NO 42
<211> LENGTH: 17
<212> TYPE: PRT
<213> ORGANISM: Artificial sequence
<220> FEATURE:
<223> OTHER INFORMATION: substituted CDR

<400> SEQUENCE: 42

Gln Ile Asn Ser Thr Gly Asn Ser Thr Tyr Tyr Pro Asp Thr Val Lys
1               5                   10                  15
```

Gly

<210> SEQ ID NO 43
<211> LENGTH: 17
<212> TYPE: PRT
<213> ORGANISM: Artificial sequence
<220> FEATURE:
<223> OTHER INFORMATION: substituted CDR

<400> SEQUENCE: 43

Gln Ile Asn Ala Val Gly Asn Ser Thr Tyr Tyr Pro Asp Thr Val Lys
1               5                   10                  15

Gly

<210> SEQ ID NO 44
<211> LENGTH: 17
<212> TYPE: PRT
<213> ORGANISM: Artificial sequence
<220> FEATURE:
<223> OTHER INFORMATION: substituted CDR

<400> SEQUENCE: 44

Gln Ile Asn Ser Ile Gly Asn Ser Thr Tyr Tyr Pro Asp Thr Val Lys
1               5                   10                  15

Gly

<210> SEQ ID NO 45
<211> LENGTH: 17
<212> TYPE: PRT
<213> ORGANISM: Artificial sequence
<220> FEATURE:
<223> OTHER INFORMATION: substituted CDR

<400> SEQUENCE: 45

Gln Ile Asn Ser Val Ala Asn Ser Thr Tyr Tyr Pro Asp Thr Val Lys
1               5                   10                  15

Gly

<210> SEQ ID NO 46
<211> LENGTH: 17
<212> TYPE: PRT
<213> ORGANISM: Artificial sequence
<220> FEATURE:
<223> OTHER INFORMATION: substituted CDR

<400> SEQUENCE: 46

Gln Ile Asn Ser Ser Gly Asn Ser Thr Tyr Tyr Pro Asp Thr Val Lys
1               5                   10                  15

Gly

<210> SEQ ID NO 47
<211> LENGTH: 17
<212> TYPE: PRT
<213> ORGANISM: Artificial sequence
<220> FEATURE:
<223> OTHER INFORMATION: substituted CDR

<400> SEQUENCE: 47

Gln Ile Asn Ser Pro Gly Asn Ser Thr Tyr Tyr Pro Asp Thr Val Lys
1               5                   10                  15

Gly

<210> SEQ ID NO 48

```
<211> LENGTH: 17
<212> TYPE: PRT
<213> ORGANISM: Artificial sequence
<220> FEATURE:
<223> OTHER INFORMATION: substituted CDR

<400> SEQUENCE: 48

Gln Ile Asn Ser Gln Gly Asn Ser Thr Tyr Tyr Pro Asp Thr Val Lys
1               5                   10                  15
Gly

<210> SEQ ID NO 49
<211> LENGTH: 17
<212> TYPE: PRT
<213> ORGANISM: Artificial sequence
<220> FEATURE:
<223> OTHER INFORMATION: substituted CDR

<400> SEQUENCE: 49

Gln Ile Asn Ile Val Gly Asn Ser Thr Tyr Tyr Pro Asp Thr Val Lys
1               5                   10                  15
Gly

<210> SEQ ID NO 50
<211> LENGTH: 17
<212> TYPE: PRT
<213> ORGANISM: Artificial sequence
<220> FEATURE:
<223> OTHER INFORMATION: substituted CDR

<400> SEQUENCE: 50

Gln Ile Asn Ser Arg Gly Asn His Thr Tyr Tyr Pro Asp Thr Val Lys
1               5                   10                  15
Gly

<210> SEQ ID NO 51
<211> LENGTH: 17
<212> TYPE: PRT
<213> ORGANISM: Artificial sequence
<220> FEATURE:
<223> OTHER INFORMATION: substituted CDR

<400> SEQUENCE: 51

Gln Ile Asn Ser Arg Gly Asn Asn Thr Tyr Tyr Pro Asp Thr Val Lys
1               5                   10                  15
Gly

<210> SEQ ID NO 52
<211> LENGTH: 17
<212> TYPE: PRT
<213> ORGANISM: Artificial sequence
<220> FEATURE:
<223> OTHER INFORMATION: substituted CDR

<400> SEQUENCE: 52

Gln Ile Asn Ser Arg Gly Asn Arg Thr Tyr Tyr Pro Asp Thr Val Lys
1               5                   10                  15
Gly

<210> SEQ ID NO 53
<211> LENGTH: 17
<212> TYPE: PRT
<213> ORGANISM: Artificial sequence
<220> FEATURE:
<223> OTHER INFORMATION: substituted CDR
```

<400> SEQUENCE: 53

Gln Ile Asn Ser Arg Gly Asn Ser Thr Tyr Tyr Pro Asp Pro Val Lys
1               5                   10                  15
Gly

<210> SEQ ID NO 54
<211> LENGTH: 17
<212> TYPE: PRT
<213> ORGANISM: Artificial sequence
<220> FEATURE:
<223> OTHER INFORMATION: substituted CDR

<400> SEQUENCE: 54

Gln Ile Asn Ser Val Gly Asn Ser Thr Tyr Tyr Pro Asp Lys Val Lys
1               5                   10                  15
Gly

<210> SEQ ID NO 55
<211> LENGTH: 17
<212> TYPE: PRT
<213> ORGANISM: Artificial sequence
<220> FEATURE:
<223> OTHER INFORMATION: substituted CDR

<400> SEQUENCE: 55

Gln Ile Asn Ser Val Gly Asn Ser Thr Tyr Tyr Pro Asp Ala Val Lys
1               5                   10                  15
Gly

<210> SEQ ID NO 56
<211> LENGTH: 17
<212> TYPE: PRT
<213> ORGANISM: Artificial sequence
<220> FEATURE:
<223> OTHER INFORMATION: substituted CDR

<400> SEQUENCE: 56

Gln Ile Asn Ser Val Gly Asn Ser Thr Tyr Tyr Pro Asp Glu Val Lys
1               5                   10                  15
Gly

<210> SEQ ID NO 57
<211> LENGTH: 17
<212> TYPE: PRT
<213> ORGANISM: Artificial sequence
<220> FEATURE:
<223> OTHER INFORMATION: substituted CDR

<400> SEQUENCE: 57

Gln Ile Asn Ser Val Gly Asn Ser Thr Tyr Tyr Pro Asp Thr Val Thr
1               5                   10                  15
Gly

<210> SEQ ID NO 58
<211> LENGTH: 17
<212> TYPE: PRT
<213> ORGANISM: Artificial sequence
<220> FEATURE:
<223> OTHER INFORMATION: substituted CDR

<400> SEQUENCE: 58

Gln Ile Asn Ile Arg Gly Asn Asn Thr Tyr Tyr Pro Asp Pro Val Lys
1               5                   10                  15

Gly

<210> SEQ ID NO 59
<211> LENGTH: 17
<212> TYPE: PRT
<213> ORGANISM: Artificial sequence
<220> FEATURE:
<223> OTHER INFORMATION: substituted CDR

<400> SEQUENCE: 59

Gln Ile Asn Ile Arg Gly Asn Asn Thr Tyr Tyr Pro Asp Thr Val Lys
1               5                   10                  15

Gly

<210> SEQ ID NO 60
<211> LENGTH: 17
<212> TYPE: PRT
<213> ORGANISM: Artificial sequence
<220> FEATURE:
<223> OTHER INFORMATION: substituted CDR

<400> SEQUENCE: 60

Gln Ile Asn Ile Arg Gly Asn Ser Thr Tyr Tyr Pro Asp Pro Val Lys
1               5                   10                  15

Gly

<210> SEQ ID NO 61
<211> LENGTH: 17
<212> TYPE: PRT
<213> ORGANISM: Artificial sequence
<220> FEATURE:
<223> OTHER INFORMATION: substituted CDR

<400> SEQUENCE: 61

Gln Ile Asn Ile Arg Gly Asn His Thr Tyr Tyr Pro Asp Thr Val Lys
1               5                   10                  15

Gly

<210> SEQ ID NO 62
<211> LENGTH: 17
<212> TYPE: PRT
<213> ORGANISM: Artificial sequence
<220> FEATURE:
<223> OTHER INFORMATION: substituted CDR

<400> SEQUENCE: 62

Gln Ile Asn Ile Arg Gly Lys Asn Thr Tyr Tyr Pro Asp Thr Val Lys
1               5                   10                  15

Gly

<210> SEQ ID NO 63
<211> LENGTH: 17
<212> TYPE: PRT
<213> ORGANISM: Artificial sequence
<220> FEATURE:
<223> OTHER INFORMATION: substituted CDR

<400> SEQUENCE: 63

Gln Ile Asn Ile Arg Gly Ser Asn Leu Tyr Tyr Pro Asp Thr Val Lys
1               5                   10                  15

Gly

<210> SEQ ID NO 64

```
<211> LENGTH: 17
<212> TYPE: PRT
<213> ORGANISM: Artificial sequence
<220> FEATURE:
<223> OTHER INFORMATION: substituted CDR

<400> SEQUENCE: 64

Gln Ile Asn Ile Arg Gly Thr Asn Ser Tyr Tyr Pro Asp Thr Val Lys
1               5                   10                  15
Gly

<210> SEQ ID NO 65
<211> LENGTH: 17
<212> TYPE: PRT
<213> ORGANISM: Artificial sequence
<220> FEATURE:
<223> OTHER INFORMATION: substituted CDR

<400> SEQUENCE: 65

Gln Ile Asn Ile Arg Gly Leu Asn Thr Tyr Tyr Pro Asp Thr Val Lys
1               5                   10                  15
Gly

<210> SEQ ID NO 66
<211> LENGTH: 17
<212> TYPE: PRT
<213> ORGANISM: Artificial sequence
<220> FEATURE:
<223> OTHER INFORMATION: substituted CDR

<400> SEQUENCE: 66

Gln Ile Asn Ile Arg Gly His Asn Thr Tyr Tyr Pro Asp Thr Val Lys
1               5                   10                  15
Gly

<210> SEQ ID NO 67
<211> LENGTH: 17
<212> TYPE: PRT
<213> ORGANISM: Artificial sequence
<220> FEATURE:
<223> OTHER INFORMATION: substituted CDR

<400> SEQUENCE: 67

Gln Ile Asn Ile Arg Gly Lys Glu Thr Tyr Tyr Pro Asp Thr Val Lys
1               5                   10                  15
Gly

<210> SEQ ID NO 68
<211> LENGTH: 17
<212> TYPE: PRT
<213> ORGANISM: Artificial sequence
<220> FEATURE:
<223> OTHER INFORMATION: substituted CDR

<400> SEQUENCE: 68

Gln Ile Asn Ile Arg Gly Lys Ser Thr Tyr Tyr Pro Asp Thr Val Lys
1               5                   10                  15
Gly

<210> SEQ ID NO 69
<211> LENGTH: 3
<212> TYPE: PRT
<213> ORGANISM: Mus sp.

<400> SEQUENCE: 69
```

Gly Asp Tyr
1

<210> SEQ ID NO 70
<211> LENGTH: 3
<212> TYPE: PRT
<213> ORGANISM: Artificial sequence
<220> FEATURE:
<223> OTHER INFORMATION: substituted CDR

<400> SEQUENCE: 70

Gly Pro Tyr
1

<210> SEQ ID NO 71
<211> LENGTH: 3
<212> TYPE: PRT
<213> ORGANISM: Artificial sequence
<220> FEATURE:
<223> OTHER INFORMATION: substituted CDR

<400> SEQUENCE: 71

Gly Asp Phe
1

<210> SEQ ID NO 72
<211> LENGTH: 3
<212> TYPE: PRT
<213> ORGANISM: Artificial sequence
<220> FEATURE:
<223> OTHER INFORMATION: substituted CDR

<400> SEQUENCE: 72

Gly Asp His
1

<210> SEQ ID NO 73
<211> LENGTH: 3
<212> TYPE: PRT
<213> ORGANISM: Artificial sequence
<220> FEATURE:
<223> OTHER INFORMATION: substituted CDR

<400> SEQUENCE: 73

Gly Asp Trp
1

<210> SEQ ID NO 74
<211> LENGTH: 3
<212> TYPE: PRT
<213> ORGANISM: Artificial sequence
<220> FEATURE:
<223> OTHER INFORMATION: substituted CDR

<400> SEQUENCE: 74

Gly Asp Ser
1

<210> SEQ ID NO 75
<211> LENGTH: 3
<212> TYPE: PRT
<213> ORGANISM: Artificial sequence
<220> FEATURE:
<223> OTHER INFORMATION: substituted CDR

<400> SEQUENCE: 75

Gly Asp Arg

<210> SEQ ID NO 76
<211> LENGTH: 3
<212> TYPE: PRT
<213> ORGANISM: Artificial sequence
<220> FEATURE:
<223> OTHER INFORMATION: substituted CDR

<400> SEQUENCE: 76

Gly Asp Val
1

<210> SEQ ID NO 77
<211> LENGTH: 112
<212> TYPE: PRT
<213> ORGANISM: Artificial Sequence
<220> FEATURE:
<223> OTHER INFORMATION: light chain

<400> SEQUENCE: 77

Asp Ile Val Met Thr Gln Thr Pro Leu Ser Leu Ser Val Thr Pro Gly
1               5                   10                  15

Gln Pro Ala Ser Ile Ser Cys Ser Ser Ser Gln Ser Leu Ile Tyr Ser
            20                  25                  30

Asp Gly Asn Ala Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Thr Gln Ser
                85                  90                  95

Thr His Ser Pro Trp Thr Phe Gly Gly Gly Thr Lys Val Glu Ile Lys
            100                 105                 110

<210> SEQ ID NO 78
<211> LENGTH: 112
<212> TYPE: PRT
<213> ORGANISM: Artificial Sequence
<220> FEATURE:
<223> OTHER INFORMATION: heavy chain

<400> SEQUENCE: 78

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Arg Tyr
            20                  25                  30

Ser Met Ser Trp Val Arg Gln Ala Pro Gly Lys Gly Leu Glu Trp Val
        35                  40                  45

Gly Gln Ile Asn Ile Arg Gly Asn Ser Thr Tyr Tyr Pro Asp Thr Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Gly Asp Phe Trp Gly Gln Gly Thr Leu Val Thr Val Ser Ser
            100                 105                 110